US 9,086,375 B2

(12) United States Patent
Priest et al.

(10) Patent No.: US 9,086,375 B2
(45) Date of Patent: Jul. 21, 2015

(54) LASER SOURCE WITH A LARGE SPECTRAL RANGE

(71) Applicant: Daylight Solutions, Inc., San Diego, CA (US)

(72) Inventors: J. Allen Priest, Escondido, CA (US); Santino Marrone, Poway, CA (US); David Caffey, San Diego, CA (US); David Arnone, Mountain View, CA (US); Michael Pushkarsky, San Diego, CA (US)

(73) Assignee: DAYLIGHT SOLUTIONS, INC., San Diego, CA (US)

( * ) Notice: Subject to any disclaimer, the term of this patent is extended or adjusted under 35 U.S.C. 154(b) by 0 days.

(21) Appl. No.: 13/949,159

(22) Filed: Jul. 23, 2013

(65) Prior Publication Data
US 2015/0070756 A1   Mar. 12, 2015

Related U.S. Application Data

(63) Continuation-in-part of application No. 13/629,341, filed on Sep. 27, 2012, which is a continuation of
(Continued)

(51) Int. Cl.
*H01S 3/13* (2006.01)
*G01N 21/39* (2006.01)
(Continued)

(52) U.S. Cl.
CPC ............... *G01N 21/39* (2013.01); *B82Y 20/00* (2013.01); *F41H 13/0056* (2013.01); *G02B 6/4206* (2013.01); *G02B 27/10* (2013.01); *G02B 27/1006* (2013.01); *H01S 5/005* (2013.01); *H01S 5/40* (2013.01); *H01S 5/4012* (2013.01); *G01N 2021/392* (2013.01);
(Continued)

(58) Field of Classification Search
CPC ... H01S 3/0941; H01S 5/141; H01S 3/08086; H01S 3/0815; H01S 3/109; H01S 3/1611; H01S 3/09415; H01S 3/1305; H01S 5/005; H01S 5/4012; H01S 5/4062; H01S 3/005; H01S 3/0092; H01S 3/0816
USPC ................................................ 372/32, 29.016
See application file for complete search history.

(56) References Cited

U.S. PATENT DOCUMENTS

| 6,134,257 A | 10/2000 | Capasso et al. |
| 6,400,744 B1 | 6/2002 | Capasso et al. |

(Continued)

FOREIGN PATENT DOCUMENTS

WO  WO 2012/118424  * 1/2012  ......... G02B 21/0048

*Primary Examiner* — Xinning Niu
*Assistant Examiner* — Vu A Vu
(74) *Attorney, Agent, or Firm* — Roeder & Broder LLP

(57) ABSTRACT

A laser source (10) for emitting an output beam (12) along an output axis (12A) includes (i) a first laser module (16) that generates a first beam (16A); (ii) a second laser module (18) that generates a second beam (18A); (iii) a beam selector assembly (32); (iv) a first director assembly (24) that directs the first beam (16A) at the beam selector assembly (32); (v) a second director assembly (26) that directs the second beam (18A) at the beam selector assembly (32); and (vii) a control system (34) that directs power to the modules (16), (18). The beam selector assembly (32) moves between a first position in which the first beam (16A) is directed along the output axis (12A), and a second position in which the second beam (18A) is directed along the output axis (12A).

20 Claims, 12 Drawing Sheets

Related U.S. Application Data application No. 12/427,364, filed on Apr. 21, 2009, now Pat. No. 8,306,077, application No. 13/949,159, which is a continuation-in-part of application No. 13/177,332, filed on Jul. 6, 2011, now Pat. No. 8,565,275.

(60) Provisional application No. 61/674,801, filed on Jul. 23, 2012, provisional application No. 61/793,298, filed on Mar. 15, 2013, provisional application No. 61/048,764, filed on Apr. 29, 2008, provisional application No. 61/362,207, filed on Jul. 7, 2010.

(51) Int. Cl.
    *H01S 5/00*    (2006.01)
    *H01S 5/40*    (2006.01)
    *B82Y 20/00*   (2011.01)
    *F41H 13/00*   (2006.01)
    *G02B 6/42*    (2006.01)
    *G02B 27/10*   (2006.01)
    *H01S 3/23*    (2006.01)
    *H01S 5/022*   (2006.01)
    *H01S 5/062*   (2006.01)
    *H01S 5/14*    (2006.01)
    *H01S 5/34*    (2006.01)

(52) U.S. Cl.
    CPC ...... *G01N 2201/0612* (2013.01); *H01S 3/2383* (2013.01); *H01S 5/02248* (2013.01); *H01S 5/02284* (2013.01); *H01S 5/06216* (2013.01); *H01S 5/141* (2013.01); *H01S 5/3401* (2013.01); *H01S 5/4087* (2013.01)

(56) References Cited

U.S. PATENT DOCUMENTS

| | | |
|---|---|---|
| 6,770,546 B2 * | 8/2004 | Yamazaki ............... 438/487 |
| 7,218,651 B2 * | 5/2007 | Hergenhan et al. .......... 372/15 |
| 7,424,042 B2 | 9/2008 | Day et al. |
| 7,446,315 B1 * | 11/2008 | Tidwell ............... 250/338.1 |
| 7,466,734 B1 | 12/2008 | Day et al. |
| 7,492,806 B2 | 2/2009 | Day et al. |
| 7,535,656 B2 | 5/2009 | Day et al. |
| 7,535,936 B2 | 5/2009 | Day et al. |
| 7,545,838 B2 * | 6/2009 | Fontanella et al. ........... 372/26 |
| 7,733,925 B2 | 6/2010 | Pushkarsky et al. |
| 7,796,341 B2 | 9/2010 | Day et al. |
| 7,826,503 B2 | 11/2010 | Day et al. |
| 7,848,382 B2 * | 12/2010 | Weida et al. ............. 372/102 |
| 7,873,094 B2 | 1/2011 | Day et al. |
| 7,920,608 B2 | 4/2011 | Marsland, Jr. et al. |
| 8,027,094 B2 | 9/2011 | Day et al. |
| 8,050,307 B2 | 11/2011 | Day et al. |
| 8,068,521 B2 | 11/2011 | Weida et al. |
| 8,189,630 B2 | 5/2012 | Marsland, Jr. et al. |
| 8,306,077 B2 | 11/2012 | Pushkarsky et al. |
| 8,335,413 B2 | 12/2012 | Dromaretsky et al. |
| 8,442,081 B2 | 5/2013 | Marsland, Jr. et al. |
| 8,467,430 B2 | 6/2013 | Caffey et al. |
| 8,565,275 B2 | 10/2013 | Pushkarsky et al. |
| 8,780,347 B2 | 7/2014 | Kotidis et al. |
| 8,879,590 B2 | 11/2014 | Pushkarsky et al. |
| 2009/0213882 A1 * | 8/2009 | Weida et al. ............... 372/23 |
| 2011/0176565 A1 * | 7/2011 | Hutchin ..................... 372/27 |
| 2011/0222566 A1 * | 9/2011 | Weida et al. ............... 372/25 |
| 2012/0033220 A1 | 2/2012 | Kotidis et al. |
| 2013/0335797 A1 * | 12/2013 | Cooper .................. 359/199.2 |

* cited by examiner

LASER SOURCE WITH A LARGE SPECTRAL RANGE

RELATED INVENTION

This application claims priority on U.S. Provisional Application Ser. No. 61/674,801, filed Jul. 23, 2012 and entitled "LASER SOURCE WITH A LARGE SPECTRAL RANGE". This application claims priority on U.S. Provisional Application Ser. No. 61/793,298, filed Mar. 15, 2013 and entitled "LASER SOURCE WITH A LARGE SPECTRAL RANGE". As far as permitted, the contents of U.S. Provisional Application Ser. Nos. 61/674,801 and 61/793,298 are incorporated herein by reference.

This application is a continuation in part of U.S. application Ser. No. 13/629,341 filed on Sep. 27, 2012 and entitled "HIGH OUTPUT, MID INFRARED LASER SOURCE ASSEMBLY". U.S. application Ser. No. 13/629,341 is a continuation of U.S. Pat. No. 8,306,077 that issued on Nov. 6, 2012 and entitled "HIGH OUTPUT, MID INFRARED LASER SOURCE ASSEMBLY". U.S. application Ser. No. 12/427,364 claims priority on U.S. Provisional Application Ser. No. 61/048,764, filed Apr. 29, 2008 and entitled "LASER SOURCE". As far as is permitted, the contents of U.S. application Ser. Nos. 13/629,341, 12/427,364 and 61/048,764 are incorporated herein by reference.

This application is also a continuation in part of U.S. application Ser. No. 13/177,332 filed on Jul. 6, 2011 and entitled "MULTI-WAVELENGTH HIGH OUTPUT LASER SOURCE ASSEMBLY WITH PRECISION OUTPUT BEAM". U.S. application Ser. No. 13/177,332 claims priority on U.S. Provisional Application Ser. No. 61/362,207, filed Jul. 7, 2010. As far as is permitted, the contents of U.S. application Ser. Nos. 13/177,332 and 61/362,207 are incorporated herein by reference.

BACKGROUND

Lasers sources are useful in many applications. For example, laser sources that generate light in the mid infrared ("MIR") range are useful for absorption spectroscopy applications since many gases of interest have their fundamental vibrational modes in the MIR range, and thus present strong, unique absorption signatures within the MIR range. Unfortunately, many existing laser sources are not capable of accurately generating light over a broad spectral range.

SUMMARY

The present invention is directed to a laser source for emitting an output beam along an output axis, the output beam consisting of a plurality of output pulses of light, with at least some of the output pulses having a different center wavelength. In one embodiment, the laser source includes (i) a first laser module that generates a first beam when power is directed to the first laser module, (ii) a second laser module that generates a second beam when power is directed to the second laser module, (iii) a beam selector assembly, (iv) a first director assembly, (v) a second director assembly, and (vii) a control system that selectively directs power to the first laser module and the second laser module. The beam selector assembly includes a beam selector, and a selector mover that selectively moves the beam selector between a first position in which the first beam is directed along the output axis, and a second position in which the second beam is directed along the output axis. The first director assembly directs the first beam at the beam selector when the beam selector is in the first position. Similarly, the second director assembly directs the second beam at the beam selector when the beam selector is in the second position. With this design, the output beam can consists of one or more sets of sequential, wavelength specific pulses of light that span a predetermined, relatively large, output wavelength range over a relatively short period of time.

In certain embodiments, (i) the first director assembly includes a first pair of spaced apart, redirectors that are independently adjustable to reflect and redirect the first beam at the beam selector when the beam selector is in the first position; and (ii) the second director assembly includes a second pair of spaced apart, redirectors that are independently adjustable to reflect and redirect the second beam at the beam selector when the beam selector is in the second position.

Additionally, the laser source can include (i) a third laser module that generates a third beam; (ii) a fourth laser module that generates a fourth beam; (iii) a third director assembly that directs the third beam at the beam selector when the beam selector is in a third position; and (iv) a fourth director assembly that directs the fourth beam at the beam selector when the beam selector is in a fourth position. In this embodiment, the selector mover selectively moves the beam selector to the third position in which the third beam is directed along the output axis with the beam selector, and the fourth position in which the fourth beam is directed along the output axis with the beam selector.

The first laser module can include a first gain medium that generates the first beam, a first grating, a first grating mover that selectively moves the first grating to select the desired wavelength of the first beam, and a first feedback detector that provides a first feedback signal that relates to an angle of incidence of the first beam on the first grating. Similarly, the second laser module can include a second gain medium that generates the second beam, a second grating, a second grating mover that selectively moves the second grating to select the desired wavelength of the second beam, and a second feedback detector that provides a second feedback signal that relates to an angle of incidence of the second beam on the second grating. With this design, the control system can selectively direct pulses of power to the first gain medium based on the first feedback signal, and can selectively direct pulses of power to the second gain medium based on the second feedback signal.

In certain embodiments, the first feedback detector includes a plurality of encoder marks and an optical reader that monitors the encoder marks. In this embodiment, the control system selectively directs a pulse of power to the first gain medium whenever the optical reader reads a predetermined number of encoder marks. Further, the control system can determine a center wavelength of the output beam based on the feedback signal.

Further, the laser source can include a frame base that retains the first laser module and the second laser module. Further, the first laser module can include a first module frame and a first temperature controller that is positioned between the first module frame and the frame base. With this design, the first temperature controller can control the temperature of the first laser module. Similarly, the second laser module can include a second module frame and a second temperature controller that is positioned between the second module frame and the frame base. With this design, the second temperature controller can control the temperature of the second laser module.

In certain embodiments, the first module frame cantilevers away from the first temperature controller. As a result thereof, the heat path between the first module frame and the frame base is primarily through the first temperature controller.

In another embodiment, the laser source includes a source frame that defines a first chamber and a spaced apart second chamber. The laser modules are positioned in the first chamber, and at least portion of the control system is positioned in the second chamber. In this embodiment, the source frame includes a floor aperture, and a pass through electrical connector that is positioned in the floor aperture and that is sealed to the source frame. With this design, the control system can be electrically connected to the laser modules via the pass through electrical connector.

Additionally, the present invention can be directed to an assembly that includes the laser source that directs the output beam at a sample, and a spectrometer. Further, the present invention is directed to a sensor system for imaging an emitting gas. For example, the imaging system can include an imager that captures a thermal image, and the laser source described above. In this embodiment, the output beam is directed at the emitting gas and the output beam is backscattered near and/or absorbed by the emitting gas. With this design, when a target emitting gas is present, the gas absorbs and attenuates the backscattered light. As a result thereof, a shadow or contrast that corresponds to the emitting gas is clearly visible in the image that is captured by the imager.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1A:
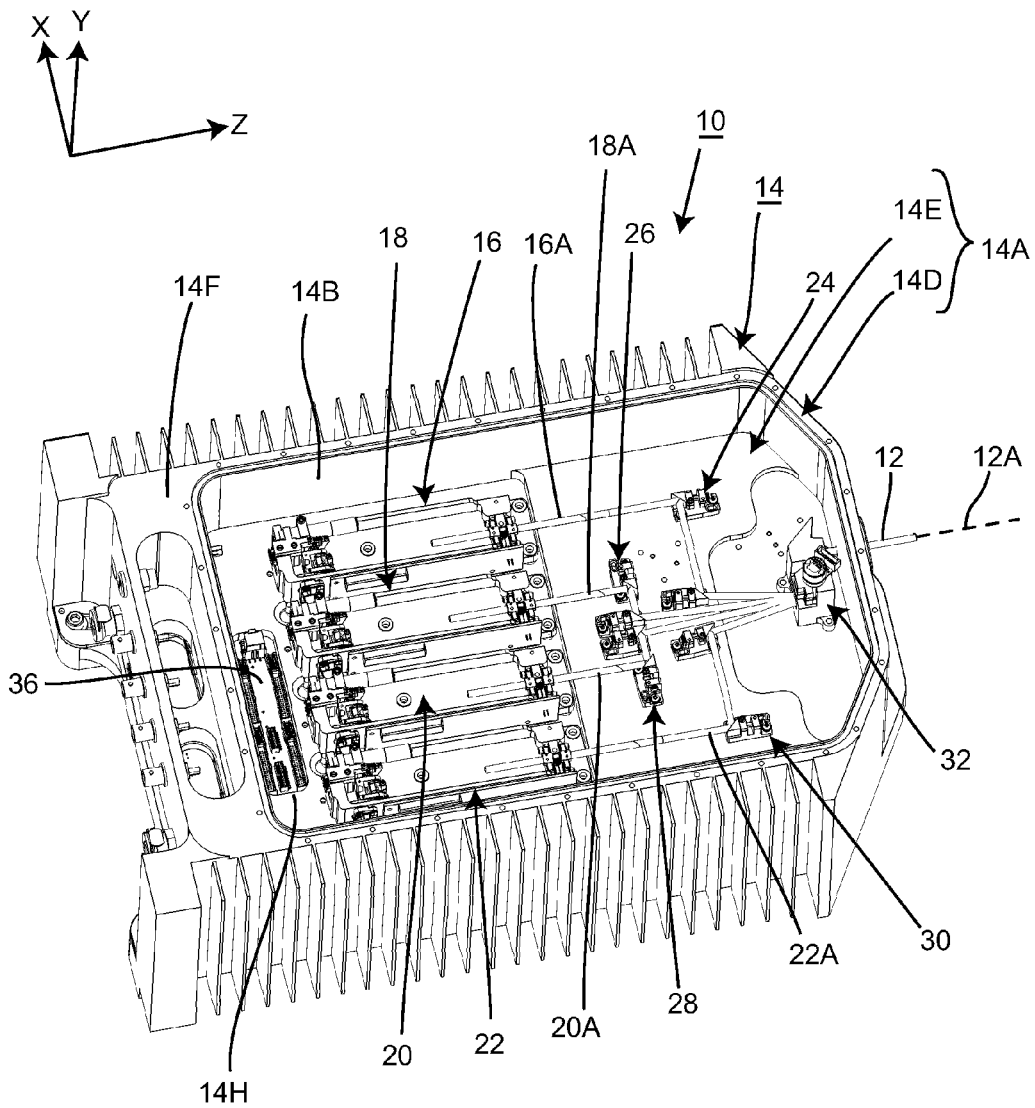
FIG. 1A is top perspective view of a laser source having features of the present invention.
Figure 1B:
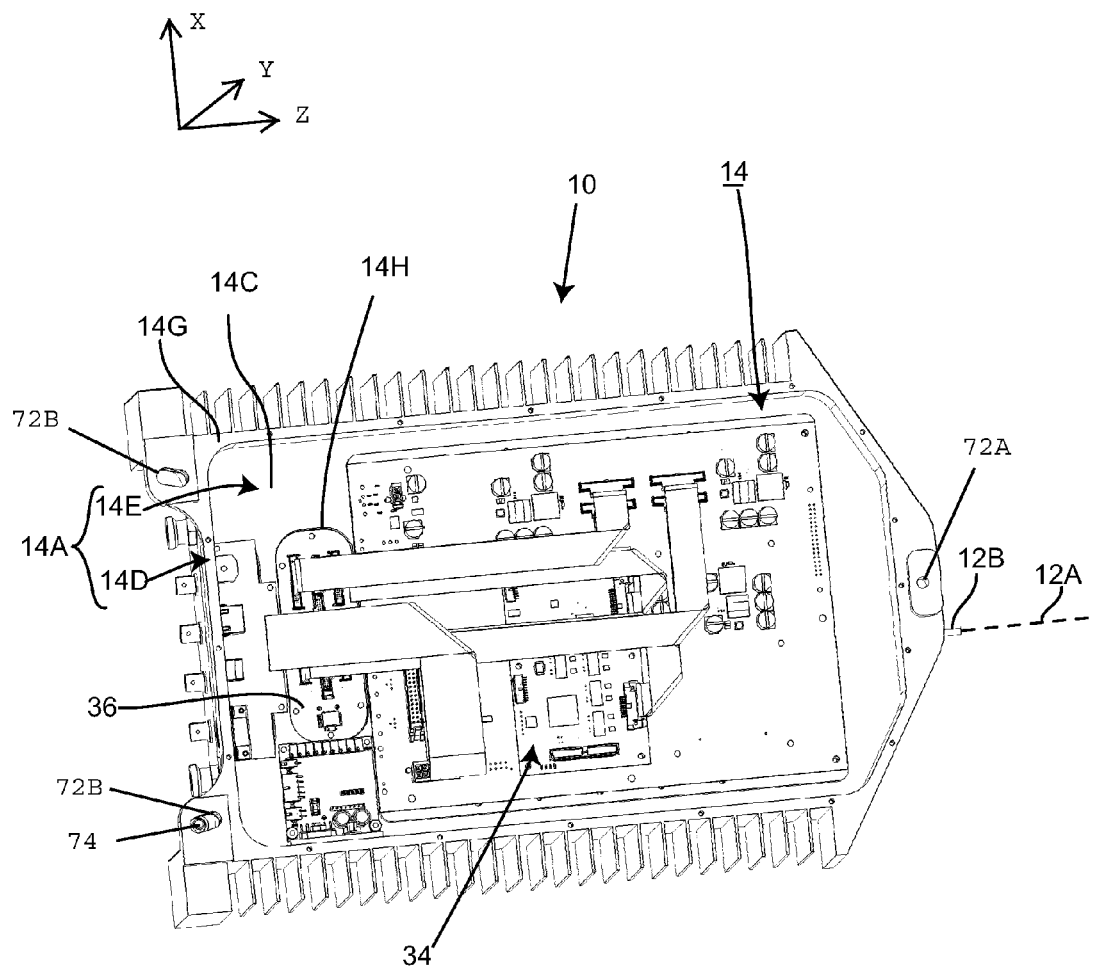
FIG. 1B is bottom perspective view of a laser source having features of the present invention.

FIG. 1A is a simplified top perspective view, and FIG. 1B is a bottom perspective view of a laser source 10 that is designed to rapidly and accurately generate an output beam 12 along an accurate and consistent output axis 12A (e.g. a Z axis). Further, in certain embodiments, the output beam 12 consists of one or more sets of sequential, wavelength specific pulses of light that span a predetermined, relatively large, output wavelength range over a relatively short period of time. For example, the laser source 10 can be used for imaging, locating, detecting, and/or identifying a substance, e.g. an emitting gas (not shown) and/or other industrial or testing applications. The laser source 10 is well suited for use with a spectrometer to provide a broad spectral sweep in a fast time because the results of the spectrometer are less influenced by heat, wind, dust, or other unstable atmospheric conditions that can distort the delivery and return paths of the output beam 12.

The desired predetermined wavelength range can be varied to suit the absorption profile/detection range of the substance being located and/or identified. In certain embodiments, a relatively large wavelength range is necessary to achieve specificity when analyzing mixtures of chemicals. Further, the resolution between different spectral signatures for different chemicals increases as the spectral range that is being analyzed is increased, thus allowing individual components to be detected.

In one embodiment, the laser source 10 is designed to generate an output beam 12 that consists of a set of sequential, specific output pulses of light having a center wavelength that span the entire or just a portion of the mid-infrared range of approximately 2-20 micrometers. With this design, the laser source 10 is particularly useful in absorption spectroscopy applications since many gases of interest have strong, unique absorption signatures within the mid-infrared range. Alternatively, the laser source 10 can be designed to generate one or more output pulses of light having a center wavelength of greater than or lesser than 2-20 micrometers.

Some of the Figures include an orientation system that illustrates an X axis, a Y axis that is orthogonal to the X axis, and a Z axis that is orthogonal to the X and Y axes. It should be noted that these axes can also be referred to as the first, second and third axes.

The design of the laser source 10 can be varied to achieve the desired type of gas detection or other usage of the laser source 10. In FIGS. 1A and 1B, the laser source 10 includes a source frame 14, a plurality of laser modules 16, 18, 20, 22, a plurality of director assemblies 24, 26, 28, 30, a beam selector assembly 32, and a control system 34 that cooperate to generate the output beam 12. The design of each of these components can be varied pursuant to the teachings provided herein. Further, it should be noted that the laser source 10 can be designed with more or fewer components than described herein.

The source frame 14 supports at least some of the components of the laser source 10. In this embodiment, the laser modules 16, 18, 20, 22; the director assemblies 24, 26, 28, 30; the beam selector assembly 32, and the control system 34 are each fixedly secured, in a rigid arrangement to the source frame 14; and the source frame 14 maintains these components in precise mechanical alignment to achieve the desired wavelength of each of the output pulses of the set. With this design, all of the critical components are fixed to the source frame 14 in a stable manner, and the laser source 10 can be self-contained and extremely portable. Alternatively, for example, the control system 34 can be separate from and external to the source frame 14.

In one embodiment, the source frame 14 includes a rigid frame base 14A; a rigid, flat, top cover (not shown) secured to the top of the frame base 14A to create an upper chamber 14B; and a rigid, flat, bottom cover (not shown) secured to the bottom of the frame base 14A to create a lower chamber 14C. In certain embodiments, the chambers 14B, 14C can be sealed to provide a controlled environment for the sensitive components of the laser source 10. For example, each chamber 14B, 14C can be filled with an inert gas, or another type of fluid, or subjected to vacuum.

The frame base 14A provides a rigid, homogeneous, one-piece platform to support the various components of the laser source 10 and to maintain the relative position of the various components of the laser source 10. In certain non-exclusive embodiments, the source frame 14A is monolithic, substantially symmetrical, and includes a generally H-shaped cross-section. In particular, the source frame 14A can include a four vertical side walls 14D that are arranged in a somewhat rectangular shaped pattern, and a base floor 14E that extends substantially horizontally between the side walls 14D. Moreover, each side wall 14D includes a side top 14F and a side bottom 14G, and the base floor 14E extends about half way between the side top 14F and the side bottom 14G of each side wall 14D. With this design, the side walls 14D function to improve the structural rigidity and stability of the base floor 14E even over temperature and pressure extremes. Further, with the present design, any changes in ambient pressure will result in equal and opposite forces on the top cover and the bottom cover that will substantially cancel out the influence on the frame base 14A due to the symmetry of the chambers 14B, 14C. This helps to maintain the desired symmetry of the frame base 14A, and thus helps to inhibit any pointing errors that may otherwise occur.

The source frame 14 can be made of a material having a thermal conductivity in the range of approximately 500-2000 W/mK, and preferably in the range of approximately 1500-2000 W/mK. Non-exclusive examples of suitable materials for the source frame 14 include magnesium, aluminum, and carbon fiber composite.

In certain embodiments, the temperature of the frame base 14A is actively maintained by circulating a circulation fluid (not shown) through internal passageways in the base floor 14E. Alternatively, the temperature of the frame base 14A is not actively, thermally controlled, but just the individual laser modules 16, 18, 20, 22 are individually, thermally controlled. In certain embodiments, the source frame 14A includes a plurality of fins. Alternatively, the source frame 14A can be designed without the fins.

Additionally, in certain embodiments, the source frame 14 includes a window (not shown) that allows the output beam 12 to exit, and a shutter (not shown) for safety that selectively opens and closes the window.

In the embodiment illustrated in FIGS. 1A and 1B, (i) the laser modules 16, 18, 20, 22; the director assemblies 24, 26, 28, 30; and the beam selector assembly 32 are secured to the top of the base floor 14E and positioned in the upper chamber 14B; and (ii) many components of the control system 34 are secured to the bottom of the base floor 14E and positioned in the lower chamber 14C.

In one embodiment, the laser source 10 includes a pass through electrical connector 36 that allows for the components of the control system 34 positioned in the lower chamber 14C to be electrically connected to the components in the upper chamber 14B while maintaining a seal between the two chambers 14B, 14C. In this embodiment, the base floor 14E includes a floor aperture 14H, and the pass through electrical connector 36 is an electrical connector that is positioned within the floor aperture 14H and sealed to the base floor 14E. The electrically connector 36 can include one or more male or female connectors. With this design, the components of the control system 34 positioned in the lower chamber 14C can be electrically connected to the pass through electrical connector 36, and the components in the upper chamber 14B can be electrically connected to the pass through electrical connector 36. With this design, many of the components of the control system 34 are sealed in a different space than the other components of the laser source 10.

The number and/or design of the laser modules 16, 18, 20, 22 can be varied pursuant to the teachings provided herein to achieve the desired output wavelength range. In one embodiment, the laser source 10 includes four, spaced apart laser modules 16, 18, 20, 22. Alternatively, the laser source 10 can be designed to include more than four, or fewer than four laser modules 16, 18, 20, 22. In one embodiment, each of the laser modules 16, 18, 20, 22 is somewhat similar in design, except for its spectral output. As provided herein, each of the laser modules 16, 18, 20, 22 can be specifically designed to generate a different portion (or partly overlapping portion) of the predetermined wavelength range. Thus, as the desired predetermined wavelength range is increased, the number of laser modules 16, 18, 20, 22 can be increased, with each laser module 16, 18, 20, 22 generating a separate portion of the predetermined wavelength range.

As provided herein, in one embodiment, power is sequentially directed to (i) the first laser module 16 to generate a first beam 16A that consists of a plurality of sequential first pulses of light that span a first range portion; (ii) the second laser module 18 to generate a second beam 18A that consists of a plurality of sequential second pulses of light that span a second range portion; (iii) the third laser module 20 to generate a third beam 20A that consists of a plurality of sequential third pulses of light that span a third range portion; and (iv) the fourth laser module 24 to generate a fourth beam 24A that consists of a plurality of sequential fourth pulses of light that span a fourth range portion. With this design, the first beam 16A, the second beam 18A, the third beam 20A, and the fourth beam 22A can be sequentially used to provide the pulses of light that cover the entire predetermined wavelength range. It should be noted that the order of firing of the laser modules 16, 18, 20, 22 can be any arrangement.

In certain embodiments, the control system 34 sequentially directs power to the laser modules 16, 18, 20, 22 in a pulsed fashion. However, in another embodiment, the control system 34 can sequentially direct power to the laser modules 16, 18, 20, 22 in a continuous fashion. In yet another embodiment, the control system 34 can simultaneously direct power to the laser modules 16, 18, 20, 22 in a continuous fashion or a pulsed fashion. This embodiment is possible because of the actively cooled frame base 14A. Further, with this latest embodiment, the beam selector assembly 32 can quickly select the output from the various laser modules 16, 18, 20, 22 to quickly select four alternative wavelengths for the output.

As a specific, non-exclusive example, (i) the first range portion can be approximately 6.5 to 7.5 micrometers; (ii) the second range portion can be approximately 7.5 to 8.5 micrometers; (iii) the third range portion can be approximately 8.5 to 9.5 micrometers; and (iv) the fourth range portion can be approximately 9.5 to 10.5 micrometers. In this example, each beam 16A, 18A, 20A, 22A has a center wavelength in the MIR range.

In one embodiment, each laser module 16, 18, 20, 22 is an extended cavity, mid infrared laser. A suitable laser module 16 is described in more detail with reference to FIG. 2A below.

In certain embodiments, because the laser modules 16, 18, 20, 22 are sequentially operated, less power is consumed, and less heat is generated than if all of the modules 16, 18, 20, 22 are powered at once. This simplifies the thermal management of the system.

As provided herein, in certain embodiments, for each laser modules 16, 18, 20, 22 there is a corresponding director assembly 24, 26, 28, 30. More specifically, (i) a first director assembly 24 is used to precisely direct the first beam 16A from the first laser module 16 at the beam selector assembly 32; (ii) a second director assembly 26 is used to precisely direct the second beam 18A from the second laser module 18 at the beam selector assembly 32; (iii) a third director assembly 28 is used to precisely direct the third beam 20A from the third laser module 20 at the beam selector assembly 32; and (iv) a fourth director assembly 30 is used to precisely direct the fourth beam 22A from the fourth laser module 22 at the beam selector assembly 32. The design of each director assembly 24, 26, 28, 30 can be varied pursuant to the teachings provided herein. Suitable beam director assemblies 24, 26, 28, 30 are described in more detail with reference to FIGS. 3A-3C.

The beam selector assembly 32 selectively and alternatively directs one of the beams 16A, 18A, 20A, 22A along the output axis 12A to provide the output beam 12. A suitable beam selector assembly 32 is described in more detail with reference to FIGS. 4A-4D.

The control system 34 controls at least a portion of the operation of the laser source 10. For example, the control system 34 can include one or more processors and circuits. In certain embodiments, the control system 34 can control the current that is directed to each laser module 16, 18, 20, 22, and the beam selector assembly 32 to control the wavelength of the output beam 12.

Figure 2A:
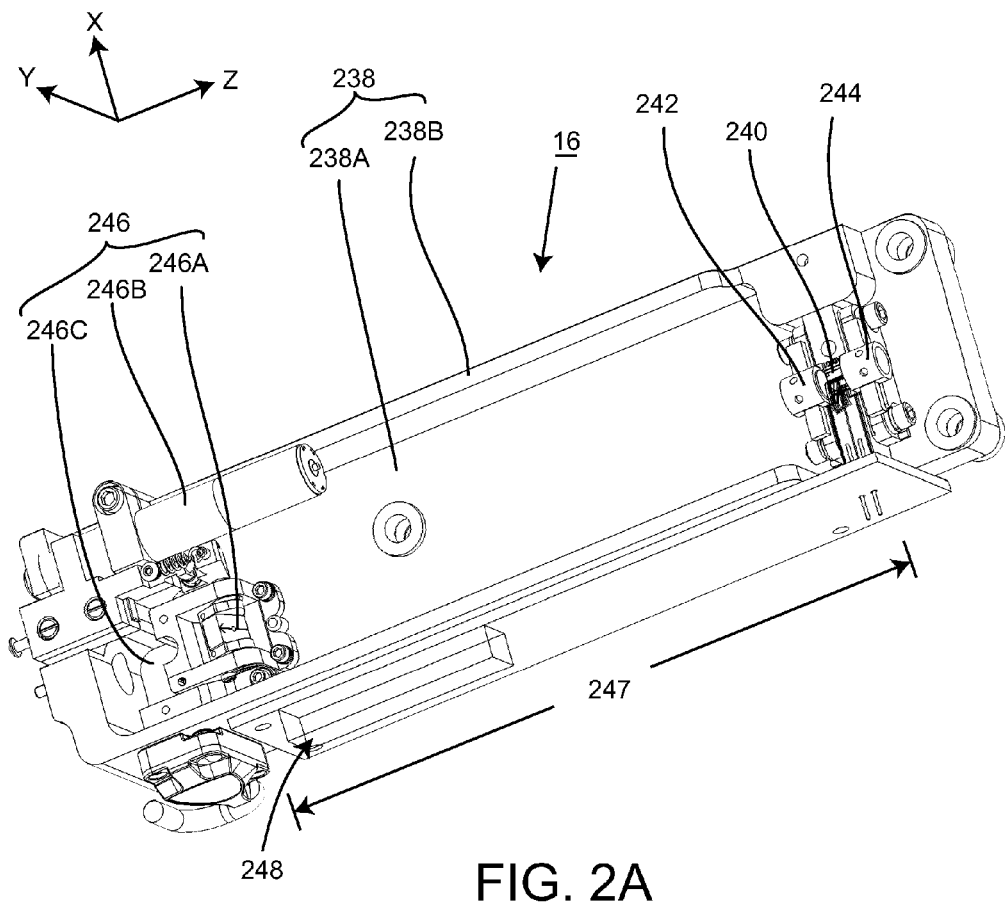
FIG. 2A is a perspective view of a laser module having features of the present invention.

FIG. 2A is a perspective view of one of the laser modules, e.g. the first laser module 16 in more detail. It should be noted that one or more of the other laser modules 18, 20, 22 can be similar in design. In the embodiment illustrated in FIG. 1A, each of the laser modules 16, 18, 20, 22 is similar in design.

In FIG. 2A, the laser module 16 includes a module frame 238, a gain medium 240, a cavity optical assembly 242, an output optical assembly 244, a wavelength dependent ("WD") feedback assembly 246, and a module controller 248. The design of each of these components can be varied.

The module frame 238 provides a rigid support for the components that are part of the laser module 16. In FIG. 2A, the module frame 238 has a cross-sectional shape that is somewhat rectiliner "U" shaped, and includes a generally flat module base 238A, and a pair of module sides 238B. In one embodiment, the module frame 238 is a single mechanical ground plane that provides structural integrity. In certain embodiments, the module frame 238 is made of rigid material that has a relatively high thermal conductivity. In one non-exclusive embodiment, the module frame 238 has a thermal conductivity of at least approximately 150 watts/meter K. With this design, in addition to rigidly supporting the components of the laser module 16, the module frame 238 also readily transfers heat away from the gain medium 240. For example, the module frame 238 can be fabricated from a single, integral piece of copper, copper-tungsten or other material having a sufficiently high thermal conductivity.

The design of the gain medium 240 can be varied pursuant to the teachings provided herein. In one, non-exclusive embodiment, the gain medium 240 for each laser module 16, 18, 20, 22 (illustrated in FIG. 1A) directly emits the respective beams 16A, 18A, 20A, 22A (illustrated in FIG. 1A) without any frequency conversion in the mid infrared range. As non-exclusive examples, the gain medium 240 for one or more of the laser modules 16, 18, 20, 22 can be a Quantum Cascade (QC) gain medium, an Interband Cascade (IC) gain medium, or a mid-infrared diode. As an example, the gain medium 240 can have a chip length of approximately 3 mm.

As provided herein, the fabrication of each gain medium 240 can be altered to achieve the desired output frequency range for each gain medium 240. For example, the gain medium 240 of the first laser module 16 can be fabricated to have a tuning range that matches the desired first range portion; the gain medium 240 of the second laser module 18 can be fabricated to have a tuning range that matches the desired second range portion; the gain medium 240 of the third laser module 20 can be fabricated to have a tuning range that matches the desired third range portion; and the gain medium 240 of the fourth laser module 22 can be fabricated to have a tuning range that matches the desired fourth range portion. As a non-exclusive example, the thickness of the wells/barriers of a Quantum Cascade gain medium determine the wavelength characteristic of the respective Quantum Cascade gain medium. Thus, fabricating a Quantum Cascade gain medium of different thickness enables production of the laser having different output frequencies within the MIR range.

With the present invention, a number of alternative laser modules can be fabricated and tested to determine their respective spectral range. Subsequently, during the assembly of the laser source 10, the laser modules that have the desired spectral ranges can be selected to achieve the desired spectral range of the laser source 10. With this design, the laser source 10 is a plug and play type system in which laser modules can selected and/or swapped (interchangeable) based on the desired spectral range.

In this embodiment, each gain medium 240 includes (i) a first facet that faces the respective cavity optical assembly 242 and the feedback assembly 246, and (ii) a second facet that faces the output optical assembly 244, and each gain medium 240 emits from both facets. In one embodiment, each first facet is coated with an anti-reflection ("AR") coating, and each second facet is coated with a reflective coating. The AR coating allows light directed from the gain medium 240 at the first facet to easily exit as a beam directed at the feedback assembly 246; and allows the light beam reflected from the feedback assembly 246 to easily enter the gain medium 240.

The beams 16A, 18A, 20A, 22A (illustrated in FIG. 1A) that exit from the respective second facet are redirected by the respective beam director assembly 24, 26, 28, 30 (illustrated in FIG. 1A). The partly reflective coating on the second facet of each gain medium 240 reflects at least some of the light that is directed at the second facet of each gain medium 240 back into the respective gain medium 240. In one non-exclusive embodiment, the AR coating can have a reflectivity of less than approximately 2 percent, and the reflective coating can have a reflectivity of between approximately 2-95 percent.

In one embodiment, for each laser module 16, (i) the reflective coating on the second facet of the gain medium 240 acts as a first end (output coupler) of an external cavity and the feedback assembly 246 (spaced apart from the gain medium 240) defines a second end of the each external cavity. The term external cavity is utilized to designate that the WD feedback assembly 246 is positioned outside of the gain medium 240. In this embodiment, the WD feedback assembly 246 is not external to the module frame 238.

The cavity optical assembly 242 is positioned between the gain medium 240 and the feedback assembly 246 along a lasing axis. The cavity optical assembly 242 collimates and focuses the beam that passes between these components. For example, each cavity optical assembly 242 can include one or more lens. For example, the lens can be an aspherical lens having an optical axis that is aligned with the respective lasing axis.

The output optical assembly 244 is positioned between the gain medium 240 and the respective beam director assembly 24, 26, 28, 30 in line with the lasing axis to collimate and focus the respective beam 16A, 18A, 20A, 22A that exits the second facet. For example, each output optical assembly 244 can include one or more lens that are somewhat similar in design to the lens of the cavity optical assemblies 32.

The WD feedback assembly 246 reflects the beam back to the gain medium 240, and is used to precisely select and adjust the lasing frequency of the external cavity and the wavelength of the pulses of light. Stated in another fashion, the WD feedback assembly 246 is used to feed back to the gain medium 240 a relatively narrow band wavelength which is then amplified in the respective gain medium 240. In this manner, the respective beams 16A, 18A, 20A, 22A may be tuned with the WD feedback assembly 246 without adjusting the respective gain medium 240. Thus, with the external cavity arrangements disclosed herein, the WD feedback assembly 246 dictates what wavelength will experience the most gain in each laser module 16, 18, 20, 22 and thus dominate the wavelength of the beams 16A, 18A, 20A, 22A.

In one embodiment, the WD feedback assembly 246 includes a grating 246A, a grating mover 246B, and a feedback detector 246C. The grating mover 246B selectively moves (e.g. rotates about the X axis in this example) the grating 246A to rapidly adjust the lasing frequency of the gain medium 240 and quickly generate the set of pulses that make up the respective beam 16A, 18A, 20A, 22A. Further, the rotational position and/or movement of the grating 246A can be continuously monitored with the feedback detector 246C that provides for closed loop control of the grating mover 246B.

With this design, movement of the grating face surface relative to the gain medium 240 and the incident beam changes the angle of incidence of the incident beam onto the grating 246A and the wavelength of the light in the external cavity. Thus, the grating mover 246B can move the grating 246A to a plurality of alternative positions to adjust the angle of incidence 8 and the wavelength of the beam. As non-exclusive examples, for each laser module, the grating mover 246B moves the grating 246A to adjust the angle of incidence 8 over the entire adjustment range to scan the wavelength range in less than approximately 0.01, 0.1, 0.5, 1, 2, 3, 4, 5, 6, 7, 8, 9, 10, 12, 14, 16, 18, 20, or more seconds.

The feedback device 246C generates a feedback signal that relates to each position of the grating 246A and/or the angle of incidence 8 of the beam on the grating 246A. As a non-exclusive example, the feedback device 246C can be an optical encoder that includes a plurality of encoder marks, and an optical reader. As provided herein, each laser modules 16, 18, 20, 22 has its own feedback device 246C.

In certain embodiments, the control system 34 (illustrated in FIG. 1B) directs current to each laser module in a pulsed fashion or a continuous fashion. The collection of accurate spectra requires that the wavelength of the output beam 12 be precisely known as the laser source 10 is tuned. In certain embodiments, the control system 34 directs pulses of power to the respective gain medium 240 based on the feedback signal received from the feedback detector 246C. In this example, the control system 34 can direct a pulse of power to the gain medium 240 every time the optical reader reads a predetermined number of encoder marks. For example, the predetermined number can be one, two, or three encoder marks.

With this design, the control system 34 can, in sequential fashion, (i) selectively direct pulses of power to the first gain medium based on the first feedback signal, (ii) selectively direct pulses of power to the second gain medium based on the second feedback signal, (iii) selectively direct pulses of power to the third gain medium based on the third feedback signal, and (iv) selectively direct pulses of power to the fourth gain medium based on the fourth feedback signal.

With this design, each laser module 16, 18, 20, 22 can be controlled to generate a set of sequential, specific, different wavelength pulses that span a portion of the desired wavelength range or the entire the MIR range. In one non-exclusive example, each laser module 16, 18, 20, 22 can be controlled to sequentially generate approximately one thousand different wavelength output pulses that cover a detection range of approximately two micrometers in the mid-infrared range. However, the number of different pulses and the range can be different than this example.

In one embodiment, the pulsing of the power to the gain medium 240 of each laser module 16, 18, 20, 22 to be tied directly to the angular rotation by employing a phase-locked-loop (PLL) technique where the position feedback signals from the feedback detector 246C are up-converted in frequency and phase locked to the angular signals to allow the pulses of power to be fired at precise angular increments that are well characterized. These angles for each power pulse can then be converted to an accurate wavelength scale for the recorded chemical spectra. Accuracy and sensitivity are also enabled by using boxcar integration techniques with the position signals to allow the high-frequency pulsing of the laser to be analyzed in real time. This is necessary to use the full spectral range of the laser even as it is rapidly tuning.

The duration of each pulse of power directed by the control system 34 to the gain medium 240 can also be varied. In alternative, non-exclusive embodiments, control system 34 can control each pulse of power to have a duration of approximately 10, 25, 50, 75, 100, 150, 200, 300, 400, 500, 600 or 700 nanoseconds.

Additionally, each laser modules 16, 18, 20, 22 can be calibrated using a wavelength measurement device (not shown) during manufacturing to determine the correlation between the feedback signals and the wavelength of the beam. With this design, each position feedback signal of each laser modules 16, 18, 20, 22 can be corresponded to a measured center wavelength of beam. Thus, each module 16, 18, 20, 22 can be calibrated at the module level prior to installation into the system. In certain embodiments, after the modules 16, 18, 20, 22 are added to the laser source, the entire system can be recalibrated by determining the correlation between the feedback signals and wavelength of the beam.

In one embodiment, each laser module 16, 18, 20, 22 is uniquely designed to have a relatively long external cavity physical length 247. In alternative non-exclusive embodiments, the long external cavity physical length 247 of one or more of the laser module 16, 18, 20, 22 is at least approximately 15, 20, 30, 40, 50, 60, 70, 80, 90, 100, 110, or 120 millimeters.

The module controller 248 is electrically connected to the rest of the control system 34 (illustrated in FIG. 1B) and can include a processor, a driver card, and/or memory that tracks the spectral range for the respective laser module 16, and/or calibration data regarding the wavelength of the beam for each position of the grating 246A. For example, the calibration data can be accumulated during testing of each laser module after assembly. With this design, the laser source 10 is a plug and play type device in which laser modules with the desired spectral range can be added to the laser source 10, and the module controller 248 can interact with the control system 34 to provide the calibration data to the control system 34. Each tunable laser module can be individually built, tested, and calibrated (encoder positions of grating 246A corresponding to the lasing wavelength) prior to assembly of the laser source 10.

Figure 2B:
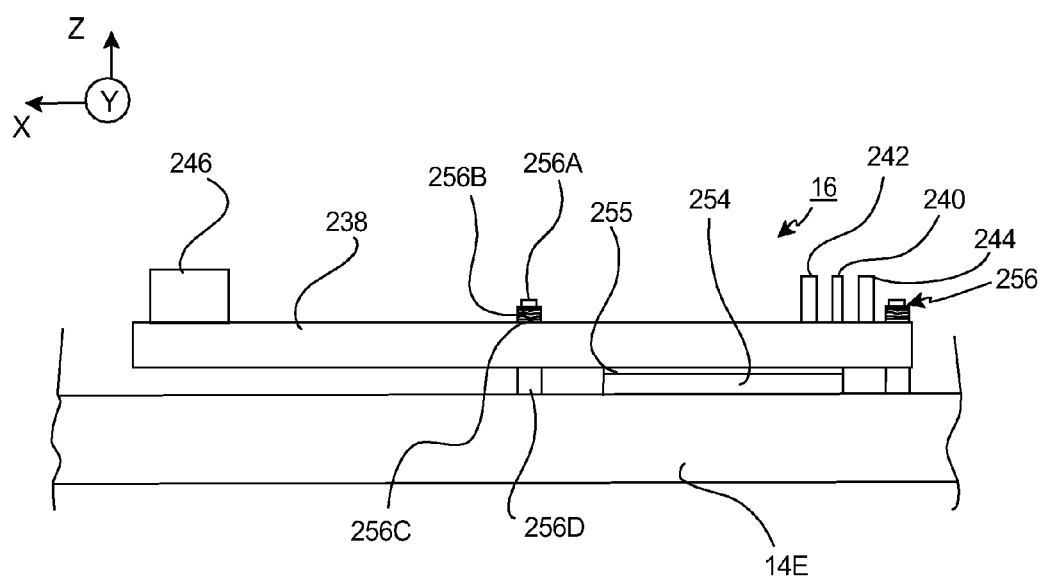
FIG. 2B is a simplified side view of a portion of the laser module and a portion of a base floor having features of the present invention.

FIG. 2B is a simplified side illustration of a portion of the laser module 16 and a portion of the base floor 14E. In this embodiment, the module frame 238, the gain medium 240, optical assemblies 242, 244, and the WD feedback assembly 246 are illustrated as simplified boxes. As provided herein, each gain medium 240 generates quite a bit of heat. In certain embodiments, each laser module 16 includes a separate temperature controller 254 to remove the heat, thereby permitting long lived operation of the laser module 16 and consistent optical output power. Further, by individually controlling the temperature of each laser module 16, the temperature controller 254 can be used to maintain the relative position of the gain medium 240 and the other components of each laser module 16.

In one embodiment, the temperature controller 254 includes a thermoelectric cooler and a temperature sensor (not shown). The thermoelectric cooler may be controlled to effect cooling or heating depending on the polarity of the drive current thereto. In one embodiment, the thermoelectric cooler is fixed to the bottom of the module frame 238 so that the thermoelectric cooler is in direct thermal communication with the module frame 238.

In certain embodiments, a compliant material 255 with a good coefficient of heat transfer is positioned between the module frame 238 and the temperature controller 254 to so that the temperature controller 254 does not deform the module frame 238 when the module frame 238 is secured to the base floor 14E. Further, graphite (not shown) can be positioned between the temperature controller 255 and the base floor 14E to provide good heat transfer and allow for some relative motion.

With the long cavity design provided herein, care it taken to inhibit mounting and/or temperature related deformation of the module frame 238 because this deformation will influence the wavelength of the beam and/or beam pointing of the module. In one embodiment, each laser module 16, 18, 20, 22 is secured to the base floor 14E in a cantilevering fashion with the only significant area of physical connection between the module frame 238 and the base floor 14E being the temperature controller 255. With this design, the primary heat path from the module frame 238 to the base floor 14E is through the temperature controller 255, with the temperature controller 255 being positioned under the primary heat source, the gain medium 240. Because there is no mechanical support for the cantilevering area, there is no direct heat flow path. With this design, the temperature controllers 255 are essentially spot cooling each of the laser modules 16, 18, 20, 22. By employing such a spot cooling methodology, the temperature controller 255 utilizes less energy because it only maintains the temperature of a relatively small module frame 238.

In alternative, non-exclusive embodiments, at least approximately 30, 40, 50, 60, 70, 80, or 90 percent of the bottom of the module frame 238 is not directly supported and is cantilevering. Thus, in non-exclusive embodiments, there is not a direct thermal path between approximately 30, 40, 50, 60, 70, 80, or 90 percent of the bottom of the module frame 238 and the base floor 14E of the source frame 14.

Further, in this embodiment, each laser module 16, 18, 20, 22 is secured to the base floor 14E with three spaced apart fastener assemblies 256. Further, each fastener assembly 256 can apply a spring tension load to the module frame 238 to get the right amount of force on compliant material 255 above temperature controller 254 without bending the module frame 238. In certain embodiments, each fastener assembly 252 includes a shoulder bolt 256A that threads into the base floor 14E, a belleville washer stack 256B, an upper thermal isolator 256C positioned between the washer stack 256B, and a lower thermal isolator 256C positioned between the module frame 238 and the base floor 14E. This reduces the transfer of heat via the fastener assemblies 256.

Figure 3A:
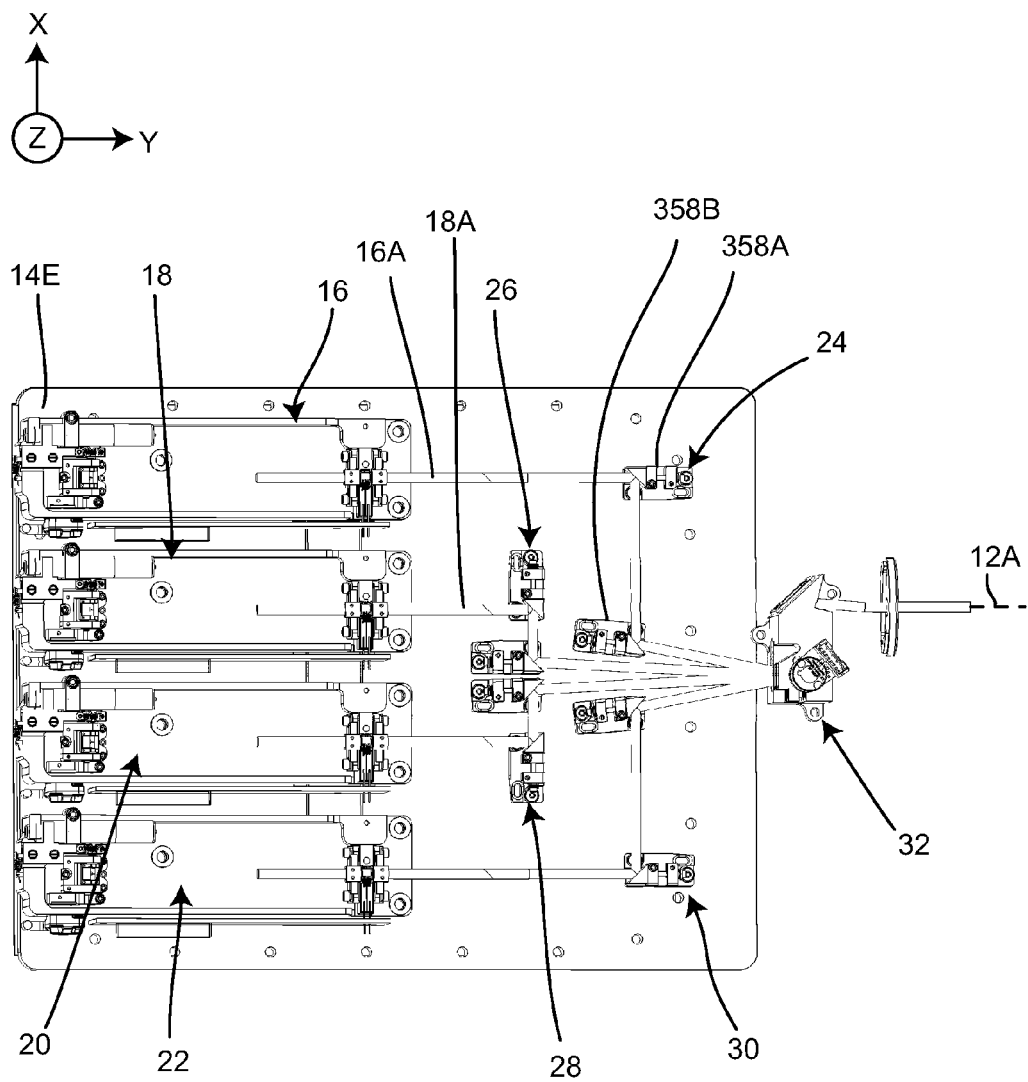
FIG. 3A is a top view of a portion of the laser source of FIGS. 1A and 1B.

FIG. 3A is a top plan view of the base floor 14E, the modules 16, 18, 20, 22, the director assemblies 24, 26, 28, 30, and the beam selector assembly 32. In this embodiment, (i) the first director assembly 24 reflects and redirects the first beam 16A at the beam selector assembly 32; (ii) the second director assembly 26 reflects and redirects the second beam 18A at the beam selector assembly 32; (iii) the third director assembly 28 reflects and redirects the third beam 20A at the beam selector assembly 32; and (iv) the fourth director assembly 30 reflects and redirects the fourth beam 22A at the beam selector assembly 32. Stated in another fashion, the beams 16A, 18A, 20A, 22A are redirected by the director assemblies 24, 26, 28, 30 to converge on the beam selector assembly 32.

In certain embodiments, with the present design, the director assemblies 24, 26, 28, 30, and the beam selector assembly 32 are designed to reflect and direct the beams 16A, 18A, 20A, 22A to maintain the polarization of the beams 16A, 18A, 20A, 22A, without rotating or changing the polarization of the beams 16A, 18A, 20A, 22A. Due to the architecture of reflective beam steering optics in a common plane with the beam selector (galvo), the laser source can have a polarization that is substantially common across the entire multi-chip range.

In one embodiment, each beam 16A, 18A, 20A, 22A is incident on the beam selector assembly 32 at approximately the same location ("selector zero point"). With the present design, the director assemblies 24, 26, 28, 30 can be used to correct the direction, pitch and yaw of the beams 16A, 18A, 20A, 22A. In one non-exclusive embodiment, each director assembly 24, 26, 28, 30 includes a pair of redirectors, namely a first redirector 358A and a second redirector 358B that is spaced apart from the first redirector 358A. In this embodiment, the pair of redirectors 358A, 358B reflect and redirect the respective beam 16A, 18A, 20A, 22A at the common, beam selector assembly 32. In one embodiment, each redirector 358A, 358B includes a mirror that redirects the respective beam 16A, 18A, 20A, 22A approximately ninety degrees. It should be noted that in one embodiment, for each module 16, 18, 20, 22, at least one of the redirectors 358A, 358B redirects the respective beam 16A, 18A, 20A, 22A at an angle that is not equal to ninety degrees.

In this embodiment, each beam 16A, 18A, 20A, 22A exits its respective laser module 16, 18, 20, 22 along the Z axis. Next, the first redirector 358A of each laser module 16, 18, 20, 22 redirects the respective beam 16A, 18A, 20A, 22A substantially along the X axis. Subsequently, the second redirector 358B of each laser module 16, 18, 20, 22 redirects the respective beam 16A, 18A, 20A, 22A substantially along (but not parallel to) the Z axis at the beam selector assembly 32.

In this embodiment, each redirector 358A, 358B is secured to the base floor 14E and each redirector 358A, 358B is independently adjustable so that the angle of incidence of each beam 16A, 18A, 20A, 22A on the beam selector assembly 32 can be selectively adjusted. For example, each redirector 358A, 358B can be independently adjustable about a first axis and about a second axis that is perpendicular to the first axis relative to the base floor 14E. For example, the first redirectors 358A can be adjustable about the X and Y axes, and the second redirectors 358B can be adjustable about the X and Z axes. With this design, the laser modules 16, 18, 20, 22 can be attached to the source frame 14, and subsequently, the redirectors 358A, 358B can be independently adjusted to achieve the desired angle of incidence of each beam 16A, 18A, 20A, 22A on the beam selector assembly 32.

Figure 3B:
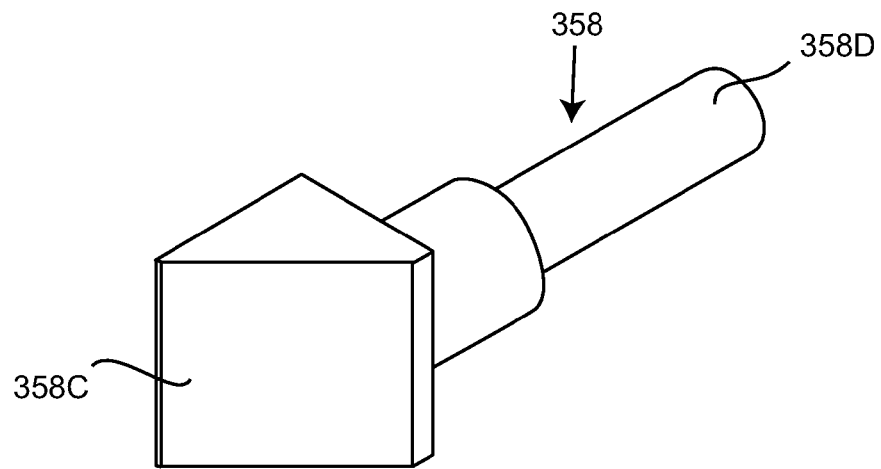
FIGS. 3B and 3C are alternative views of a the redirector having features of the present invention.
Figure 3C:
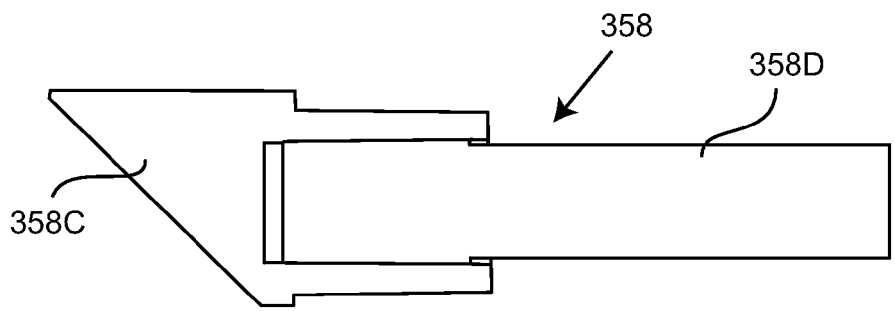
Figure 4A:
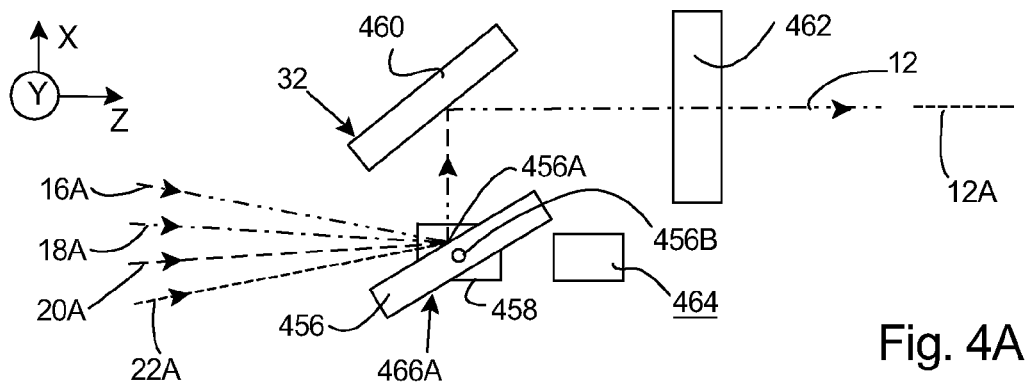
FIGS. 4A, 4B, 4C, and 4D are simplified top views of a beam selector assembly having features of the present invention.
Figure 4B:
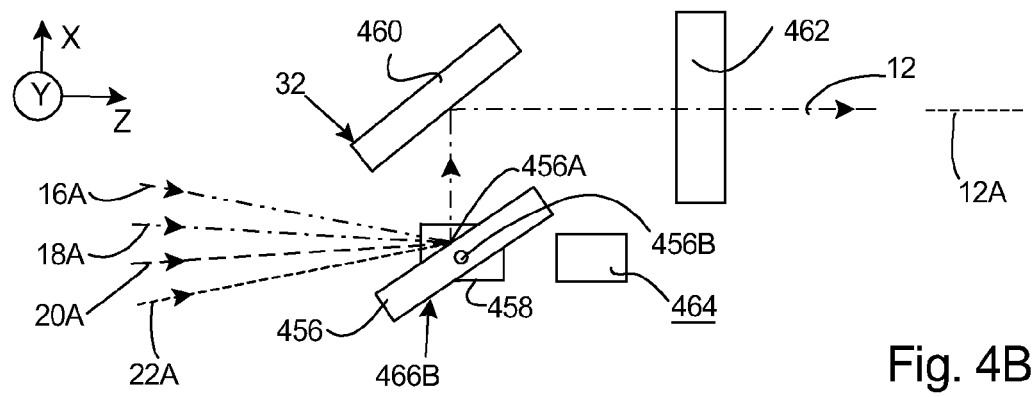
Figure 4C:
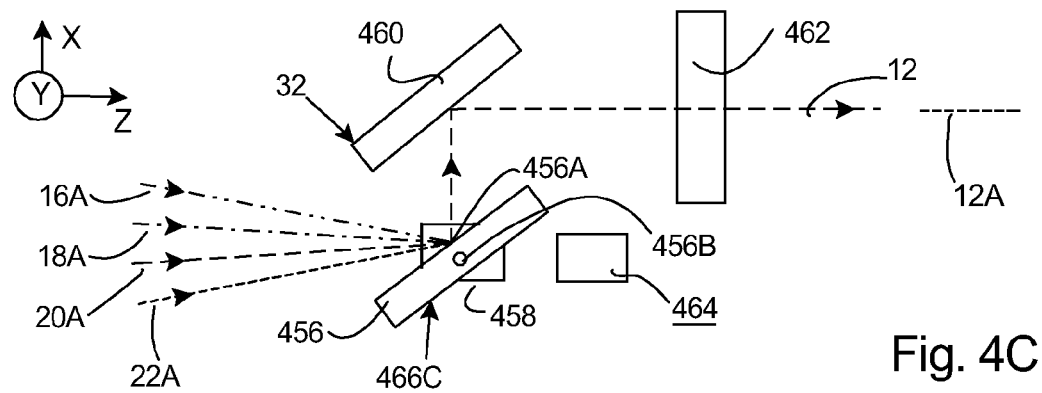
Figure 4D:
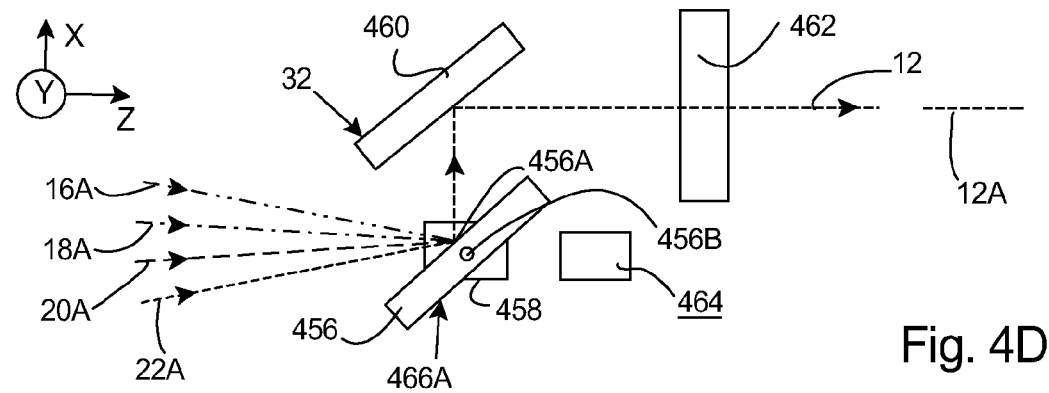

FIG. 3B is a perspective view and FIG. 3C is a cut-away view of a portion of one of the redirector 358 that can be used as a first redirector 358A, and/or the second redirector 358B. In this embodiment, the redirector 358 includes a mirror 358C the redirects the beam approximately ninety degrees, and a rod 358D that cantilevers away from the mirror 358C. Additionally, the redirector 358 includes a rod retainer (not shown in FIGS. 3B and 3C) that selectively retains the rod 358D. For example, the rod retainer can selectively retain the rod 358D with a three point clamp. In this embodiment, the rod retainer can be fixedly secured to the base floor 14E. With this design, the mirror 358C and rod 358D can be rotated about two axes and subsequently fixedly secured to the base floor 14E.

Referring back to FIG. 3A, the design of the beam selector assembly 32 can be varied pursuant to the teachings provided herein. As provided herein, the beams 16A, 18A, 20A, 22A are directed at the beam selector assembly 32, and the beam selector assembly 32 is positioned to select the desired beam 16A, 18A, 20A, 22A, and direct selected beam along the output axis 12A.

FIGS. 4A-4D are simplified top views of a beam selector assembly 32 having features of the present invention and a portion of the beams 16A, 18A, 20A, 22A, and the output beam 12. In FIGS. 4A-4D, all of the beams 16A, 18A, 20A, 22A are directed at the beam selector assembly 32 at once. This occurs when sufficient power is directed to all of the laser modules (not shown in FIGS. 4A-4B) at the same time. Typically, however, sufficient power will be directed to only one laser module (not shown in FIGS. 4A-4B) at any given time. With this example, only one of the beams 16A, 18A, 20A, 22A will be directed at the beam selector assembly 32 at any given time.

In this embodiment, the beam selector assembly 32 includes a beam selector 456, a selector mover 458, a selector redirector 460 (e.g. a turn mirror), and a selector lens 462 positioned on the output axis 12A to collimate the output beam 12. With this design, a single element (e.g. a mirror) can be moved to select the beam from multiple lasers. The design of each of these components can be varied to achieve the design requirements of the laser source.

In one embodiment, the beam selector 456 is a flat mirror having a mirror center surface 456A, and the selector mover 458 is a motor that moves (e.g. rotates) the beam selector 456 about a selector axis 456B that is substantially parallel to the Y axis. In one embodiment, the beam selector 456 and the selector mover 458 are a galvo assembly that include a flat, galvo mirror and a galvo mover that selectively moves (e.g. rotates) the galvo mirror about the Y axis) in a closed loop fashion. With this design, the movement of the beam selector 456 about a single axis (a single axis movement) is used to select the beam that is used for the output beam 12. Further, with this design, the galvo can be controlled to make real time corrections in the position of the beam selector 456 to correct if one of the beams wonders.

Additionally, the beam selector assembly 32 can include a selector feedback device 464 that additionally measures and monitors the position of the mirror 456 and provides a position signal to the control system 34 that can be used for closed loop control of the selector mover 458. As non-exclusive examples, the beam selector assembly 32 can be an optical encoder, or a Hall type sensor.

In this embodiment, the beams 16A, 18A, 20A, 22A are directed at the beam selector assembly 32 at different angles. With this design, the selector mover 458 can selectively position the beam selector 456 at alternative positions to redirect (select) one of the beams 16A, 18A, 20A, 22A at the selector redirector 460 which redirects that beam along the output axis 12A as the output beam 12. For example, (i) when the beam selector 456 is moved to a first position 466A (illustrated in FIG. 4A), the first beam 16A is directed by the beam selector 456 at the selector redirector 460 to provide the output beam 12 that is made of the first beam 16A; (ii) when the beam selector 456 is moved to a second position 466B (illustrated in FIG. 4B), the second beam 18A is directed by the beam selector 456 at the selector redirector 460 to provide the output beam 12 that is made of the second beam 18A; (iii) when the beam selector 456 is moved to a third position 466C (illustrated in FIG. 4C), the third beam 20A is directed by the beam selector 456 at the selector redirector 460 to provide the output beam 12 that is made of the third beam 20A; and (iv) when the beam selector 456 is moved to a fourth position 466D (illustrated in FIG. 4D), the fourth beam 22A is directed by the beam selector 456 at the selector redirector 460 to provide the output beam 12 that is made of the fourth beam 22A. These positions can be indexed and saved in the control system 34. With this design, the beam selector 456 can be positioned and the laser modules 16, 18, 20, 22 can be controlled to generate the desired output beam 12.

As provided herein, (i) the first director assembly 24 (illustrated in FIG. 3A) directs the first beam 16A approximately at the mirror center 456A when the beam selector 456 is in the first position 466A; (ii) the second director assembly 26 (illustrated in FIG. 3A) directs the second beam 18A approximately at the mirror center 456A when the beam selector 456 is in the second position 466B; (iii) the third director assembly 28 (illustrated in FIG. 3A) directs the third beam 20A approximately at the mirror center 456A when the beam selector 456 is in the third position 466C; and (iv) the fourth director assembly 30 (illustrated in FIG. 3A) directs the fourth beam 22A approximately at the mirror center 456A when the beam selector 456 is in the fourth position 466D.

Further, the selector mover 458 selectively moves the beam selector 456 between (i) the first position 466A in which the first beam 16A is directed along the output axis 12A, (ii) the second position 466B in which the second beam 18A is directed along the output axis 12A; (iii) the third position 466C in which the third beam 20A is directed along the output axis 12A, and (iv) the fourth position 466D in which the fourth beam 22A is directed along the output axis 12A;

In one embodiment, the beam selector 456 is a flat mirror. Alternatively, the beam selector 456 can be a multifaceted polygonal mirror (e.g. a Chinook polygonal mirror like that sold by Lincoln Laser) that is rapidly rotated by the selector mover 458.

Referring back to FIGS. 1A and 1B, the control system 34 controls the operation of the laser modules 16, 18, 20, 22, the temperature controller 254 (illustrated in FIG. 2B), and the beam selector assembly 32 to control the characteristics of the output beam 12. The control system 34 can include one or more processors and memory. As provided herein, in certain embodiment, the control system 34 directs (i) power to the laser modules 16, 18, 20, 22 so that only one of the laser modules 16, 18, 20, 22 is firing at one time, and (ii) power to the beam selector assembly 32 so that the beam selector assembly 32 directs that firing beam along the output axis 12A. With this design, one or more of the laser modules 16, 18, 20, 22 can be turned off when its beam 16A, 18A, 20A, 22A is not being used for the output beam 12.

Additionally, the laser source 10 can be calibrated using a wavelength measurement device during manufacturing of the laser source 10. More specifically, with the laser source 10 activated, each laser module 16, 18, 20, 22 can be sequentially operated while monitoring position of the respective grating, and the wavelength of the output pulses of the output beam 12 with the wavelength measurement device. With this design, the laser source 10 can be calibrated, and the control system 34 can determine a center wavelength of the output pulses of the output beam 12 based on the position signal of the respective gratings of the laser modules 16, 18, 20, 22.

Moreover, in certain embodiments, the laser source 10 can include a reference sensor (not shown) that picks off a portion of the output beam 12 for testing of the wavelength of the output beam 12.

In certain embodiments, the control system 34 is designed to support high speed buses. Further, in certain embodiments, the control system 34 can be controlled with a laptop or smart phone that is connected with a USB or wireless link.

In one embodiment, the control system 34 controls the shutdown of the laser source 10 in a unique fashion. For example, upon instructions to shutdown, the control system 34 can immediately cut power to the gain medium, while maintaining power to the controls to collect and save any necessary data and have the controller/processor have a soft landing.

Figure 5:
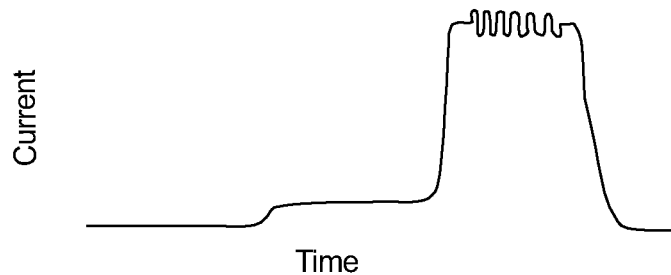
FIG. 5 is a simplified illustration of a current command.

Further, the control system 34 can direct power slightly below what is required to lase the on-deck (next activated) laser module 16, 18, 20, 22 just prior to it being used for the output beam 12 to allow for quick transitions (switch times) between laser modules 16, 18, 20, 22. This reduces the time required to achieve beam stability when transitioning between laser modules 16, 18, 20, 22. FIG. 5 is a simplified, non-exclusive example of a current command that can be directed by the control system 34 to one of the laser modules 16, 18, 20, 22. In this example, the current is initially zero. Subsequently, the current can be slightly increased to pretrigger the laser module. Next, the current can be directed to the laser module in a pulsed fashion. With this design, the pretrigger step reduces the delay, improves turn-on time, and results in more consistent turn-on times for the laser modules.

Referring back to FIG. 1B, in certain embodiments, the source frame 14 is designed to be mounted to an optical bench 670 (illustrated in FIG. 6) in a fashion that allows the source frame 14 to expand and contract relative to optical bench 670 without distorting the source frame 14. In one embodiment, the source frame 14 includes a front aperture 72A, and a spaced apart pair of rear slots 72B. With this design, a front fastener (not shown) can extend through the front aperture 72A and thread into the optical bench 670 to hold the position of the source frame 14 and the alignment of the output beam 12B relative to the optical bench. Further, a pair of rear fastener assemblies 74 (only one is illustrated in FIG. 1B) extend through the rear slots 72B and thread into the optical bench 670. It should be noted that the spacing of the front aperture 72A and the rear slots 72B can be suited to accommodate both English or metric tables.

Figure 6:
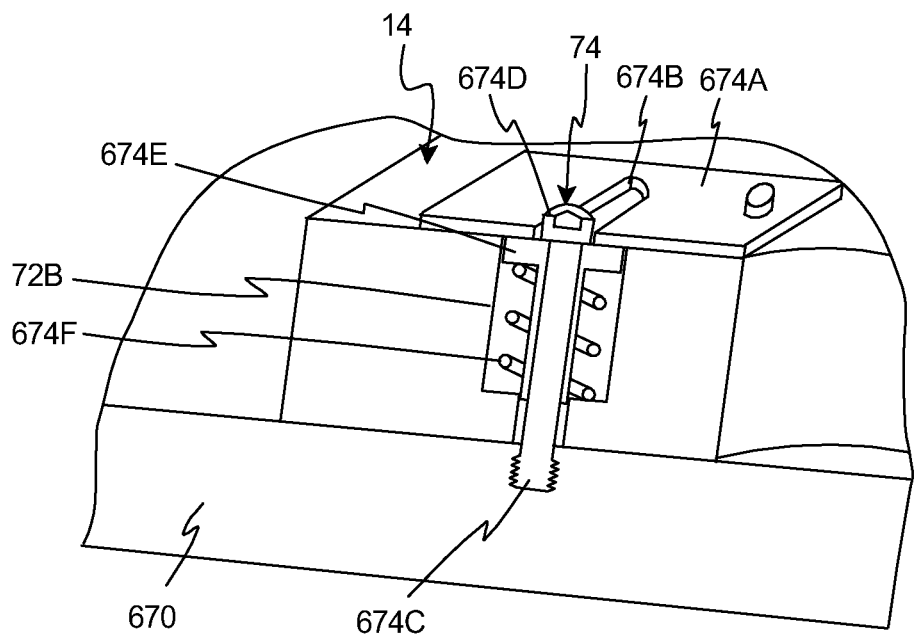
FIG. 6 is a simplified cut-away view of a portion of an optical bench, and a portion of a laser source having features of the present invention.

FIG. 6 is a simplified cut-away view of a portion of the optical bench 670, a portion of the source frame 14, one of the rear slots 72B, and one of the rear fastener assemblies 74. The optical bench 670 can be a table, test bench or test stand.

In this embodiment, the rear fastener assembly 74 includes (i) an upper plate 674A that secured to the source frame 14, the upper plate 674A including a plate slot 674B, (ii) a fastener 674C that is positioned in rear slot 72B and that threaded into the optical bench 670, the fastener 674C including a fastener head 674D that slides in the plate slot 674B; (iii) a fastener sleeve 674E that is positioned on the fastener 674C, and (iv) a resilient member 674F that urges the fastener sleeve 674E upward. With this design, the rear fastener assembly 74 urges the source frame 14 downward, while allowing the source frame 14 to slide relative to the optical bench 670 during expansion or contraction.

Figure 7:
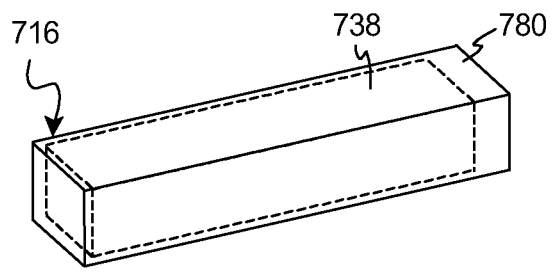
FIG. 7 is a simplified perspective view of another embodiment of a laser module having features of the present invention.

FIG. 7 is a simplified perspective view of another embodiment of a laser module 716 having features of the present invention. In this embodiment, the module frame 738 and the other components of the laser module 716 are encased (surrounded) with an isothermal barrier 780. For example, the isothermal barrier 780 can be machinable foam. In this embodiment, the isothermal foam covers the rest of the module 716 and can include a hole (not shown) for the beams to travel. The isothermal barrier 780 shields the laser module 716 from parasitic heat loading of the laser module 716 from the environment within the laser source. In certain embodiments, the isothermal barrier 780 is made of a closed cell foam, or a foam that is sealed to inhibit the absorption of water.

In FIG. 7, each laser module 716 (only one is show) is enclosed with an individual barrier 780. Alternatively, a single barrier can enclose a plurality of laser modules 716.

Figure 8:
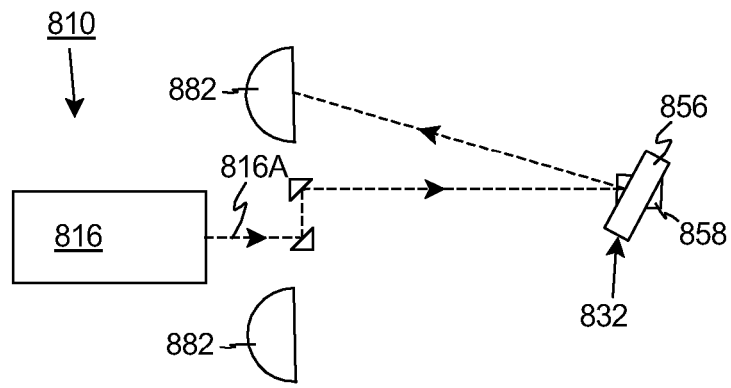
FIG. 8 is simplified illustration of a portion of yet another embodiment of the laser source.

FIG. 8 is simplified illustration of a portion of another embodiment of the laser source 810. Only one of the laser modules 816 is illustrated in this simplified example. However, it should be noted that the laser source 810 can include multiple laser modules. In this embodiment, the beam 816A from the laser module 816 can be alternatively redirected by the beam selector assembly 856 (including the beam selector 856 and the selector mover 858) to one or more sensors 882 (e.g. photodetectors and two are illustrated in FIG. 8). With this design, the sensors 882 can be used by the control system for calibrating and aligning the beam selector 856 for improved accuracy. The two sensors 882 will allow for gain and offset calibrations.

Figure 9:
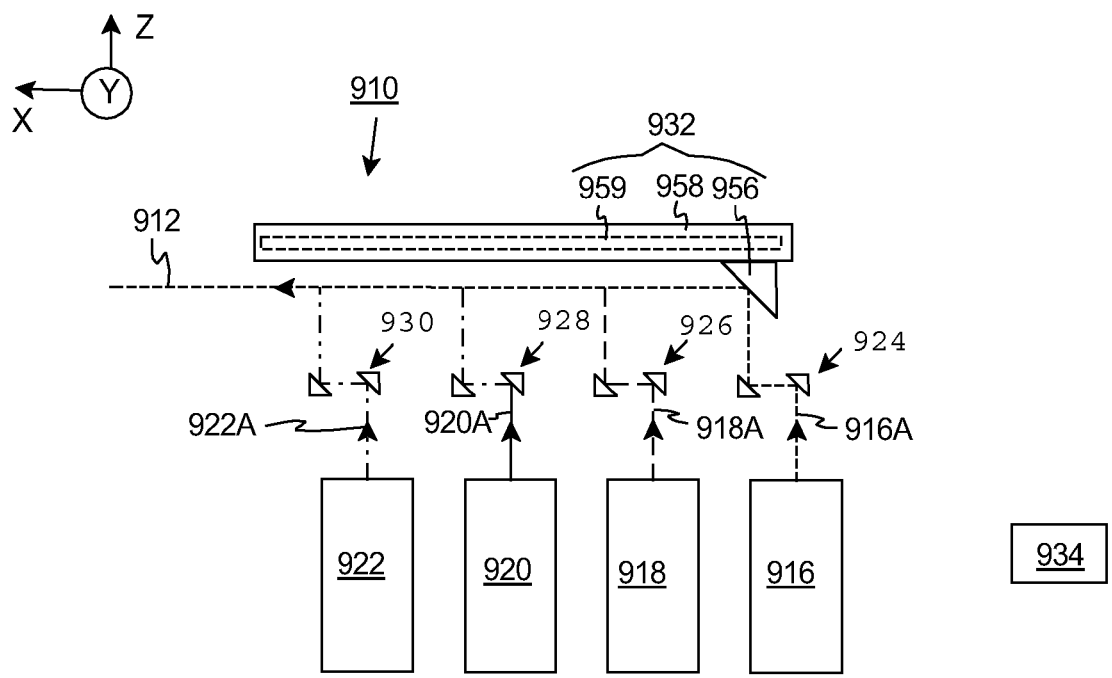
FIG. 9 is a simplified top view of still another embodiment of a laser source.

FIG. 9 is a simplified top view of yet another embodiment of a laser source 910 including four laser modules 916, 918, 920, 922, that generate beams 916A, 918A, 920A, 922A, the corresponding director assemblies 924, 926, 928, 930, and the control system 934 are similar to the corresponding components described above. However, in this embodiment, the beam selector assembly 932 is slightly different. More specifically, in this embodiment, the beam selector assembly 932 includes (i) a beam selector 956 that can be mirror; (ii) a selector mover 958 that moves the beam selector 956 linearly (e.g. along the X axis); and (iii) a linear guide 959 (illustrated in phantom) that guides the motion of the beam selector 956 along an axis. With this design, the beam selector 956 can be moved to individually select the 916A, 918A, 920A, 922A as the output beam 912.

Figure 10:
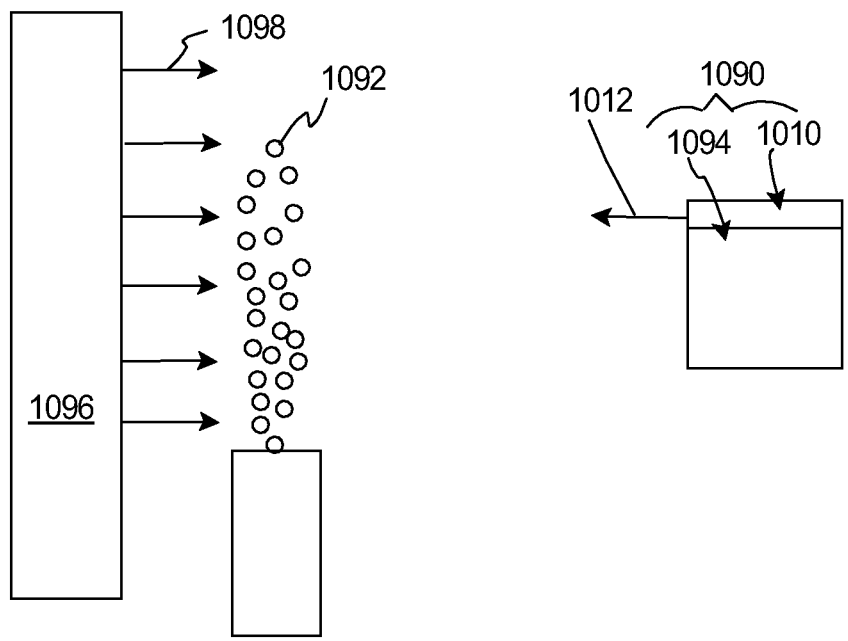
FIG. 10 is simplified illustration of a substance sensor system having features of the present invention.

FIG. 10 is simplified illustration of a substance sensor system 1090 having features of the present invention and a substance 1092 e.g. an emitting gas. In this embodiment, the sensor system 1090 includes (i) a laser source 1010 similar to that disclosed herein that generates an output beam 1012 that illuminates the area near the emitting gas 1092, and (ii) an imager 1094 (i.e. an infrared camera) that captures real-time, high resolution thermal images of the emitting gas 1092 that can be displayed or recorded for future viewing. As non-exclusive examples, the sensor system 1090 is useful for locating substances 1092 (i.e. leaks) in the oil, gas, utility, chemical industries, as well as locating emitting gas for homeland security. In one embodiment, the type of substance 1092 detectable by the sensor system 1090 can include any gas having molecules that absorb ("absorption features") in the MIR range.

Figure 11:
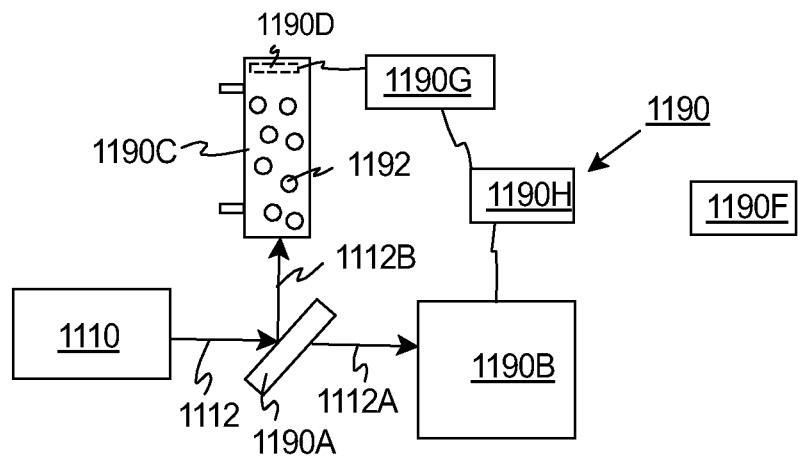
FIG. 11 is simplified illustration of another embodiment of a sensor system having features of the present invention.

FIG. 11 is simplified illustration of another embodiment of a sensor system having features of the present invention. In this embodiment, the sensor system includes a laser source 1110 (similar to those described above) that generates an output beam 1112 consisting of a plurality of output pulses, and a spectrometer 1190 that utilizes the output pulses to analyze one or more substance 1192 (illustrated as circles). For example, the substance 1192 can be a liquid, gas or solid.

In this embodiment, the spectrometer 1190 includes (i) a beam splitter 1190A that splits the output beam 1112 into two beams 1112A, 1112B, (ii) a reference detector 1190B that receives one of the beams 1112A and that analyzes the beam 1112A to determine the unattenuated power level, (iii) a sample area 1190C (e.g. a container) that receives the other beam 1112B and the one or more gases 1192, (iv) a signal detector 1190D (illustrated in phantom) that detects the beam 1112B after traveling through the sample area 1190C, (v) control electronics 1190F for powering the laser 1110 and the spectrometer 1190, (vi) acquisition electronics 1190G for digitizing and integrating the detector signals from the signal detector 1190D, and (vii) analysis electronics 1190H for assembling the data into spectra and analyzing the spectra to determine the concentration and/or presence of different chemicals in the gases 1192.

For example, the sample area 1190C can be a container that receives the one or more substances 1192. The sample area 1190C can include an area input and an area output that allows the substances 1192 to be changed. In alternative embodiments, the sample area 1190C receives a gas or condensed phase sample in a cell, or a condensed phase sample in an attenuated-total-reflectance (ATR) device.

Figure 12:
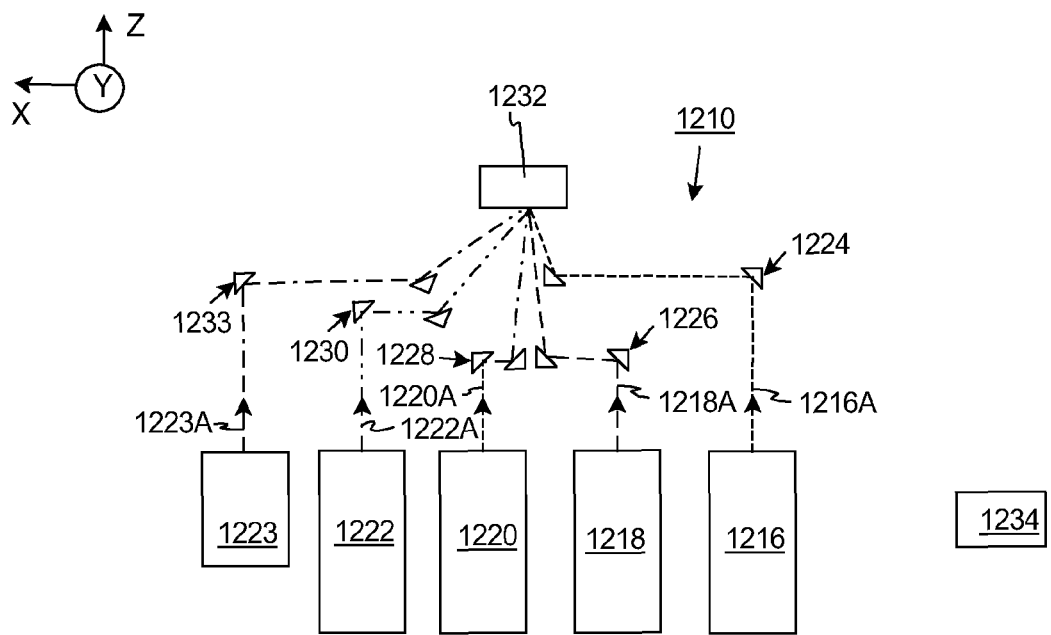
FIG. 12 is a simplified top view of yet another embodiment of a laser source having features of the present invention.

FIG. 12 is a simplified top view of yet another embodiment of a laser source 1210 that includes four laser modules 1216, 1218, 1220, 1222 that generate beams 1216A, 1218A, 1220A, 1222A, the corresponding director assemblies 1224, 1226, 1228, 1230, the beam selector assembly 1232, and the control system 1234 that are somewhat similar to the corresponding components described above and illustrated in FIG. 3A. However, in this embodiment, the laser source 1210 includes a pilot laser module 1223 that generates a visible laser beam 1223A that is directed at the beam selector assembly 1232 with a director assembly 1233 (similar to other director assemblies). With this design, the beam selector assembly 1232 can select the visible laser beam 1223A that can be used for visually alignment of the laser source 1210 with the other components of system.

Figure 13:
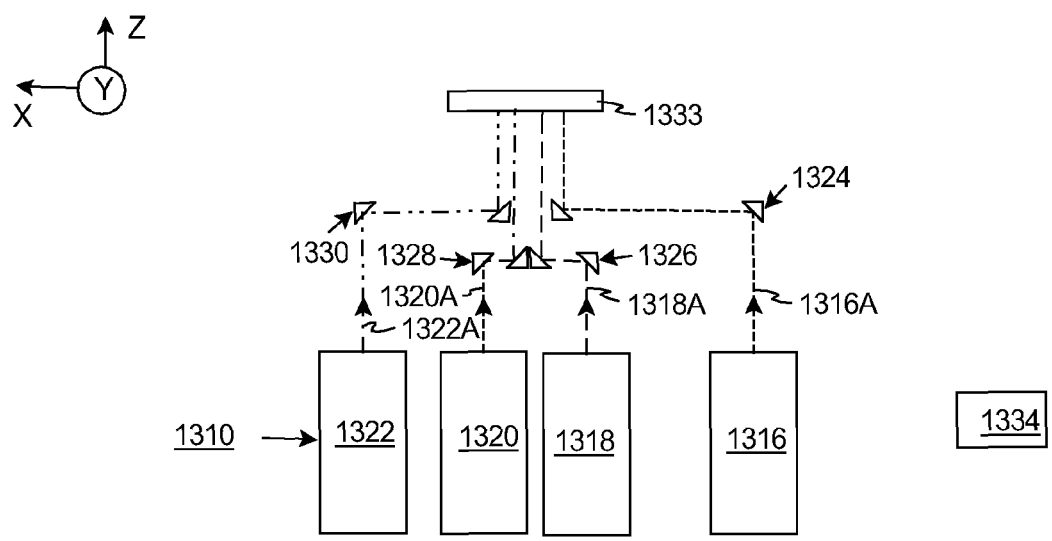
FIG. 13 is a simplified top view of still another embodiment of a laser source having features of the present invention.

FIG. 13 is a simplified top view of yet another embodiment of a laser source 1310 that includes four laser modules 1316, 1318, 1320, 1322, that generate beams 1316A, 1318A, 1320A, 1322A, the corresponding director assemblies 1324, 1326, 1328, 1330, and the control system 1234 that are somewhat similar to the corresponding components described above and illustrated in FIG. 3A. However, in this embodiment, there is no the beam selector assembly. Instead, in this embodiment, the director assemblies 1324, 1326, 1328, 1330 direct the beams 1316A, 1318A, 1320A, 1322A at a combiner lens 1333 that focuses the beams 1316A, 1318A, 1320A, 1322A.

In this embodiment, the director assemblies 1324, 1326, 1328, 1330 direct and steer the beams 1316A, 1318A, 1320A, 1322A at the combiner lens 1333 in a substantially parallel arrangement with a combiner axis of the combiner lens 1333. Stated in another fashion, the director assemblies 1324, 1326, 1328, 1330 combine the beams 1316A, 1318A, 1320A, 1322A by directing the beams 1316A, 1318A, 1320A, 1322A to be parallel to each other (e.g. travel along parallel axes), directed in the same direction, with the beams 1316A, 1318A, 1320A, 1322A partly or fully overlapping, or adjacent to each other.

In this embodiment, the beams 1316A, 1318A, 1320A, 1322A are steered to co-propagate parallel to each other at the distance between the beam centers of each beams 1316A, 1318A, 1320A, 1322A being close to the individual beam diameter. With this design, the beams 1316A, 1318A, 1320A, 1322A propagate along parallel axes. A more complete discussion of this type of beam combining is provided in U.S. Pat. No. 8,306,077.

Figure 14:
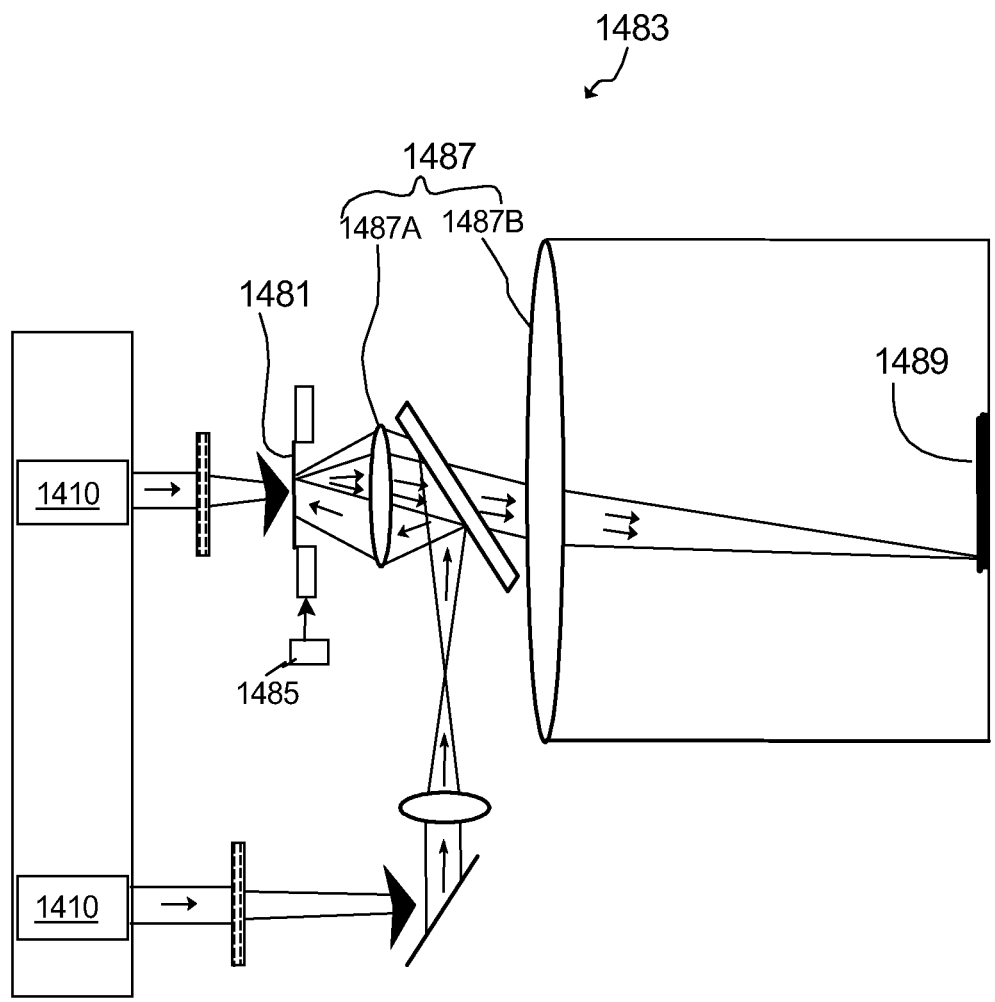
FIG. 14 is a simplified view of an microscope having features of the present invention.

FIG. 14 is a simplified schematic illustration of a sample 1481 and a non-exclusive embodiment of an imaging microscope 1483 having features of the present invention. In particular, the imaging microscope 1483 can be used to analyze and evaluate the various properties of the sample 1481. For example, in one embodiment, the imaging microscope 1483 is an infrared imaging microscope that uses tunable laser radiation to spectroscopically interrogate one or more samples 1481 in order to analyze and identify the properties of the sample.

The sample 1481 can be a variety of things, including human tissue, animal tissue, plant matter, explosive residues, powders, liquids, solids, inks, and other materials commonly analyzed using Fourier transform infrared (FTIR) microscopes. More particularly, in certain non-exclusive applications, the sample 1481 can be human tissue and the imaging microscope 1483 can be utilized for rapid screening of the tissue sample 1481 for the presence of cancerous cells and/or other health related conditions; and/or the imaging microscope 1483 can be utilized in certain forensic applications such as rapid screening of the sample 1481 for the presence of explosive residues and/or other dangerous substances.

Further, the sample 1481 can be thin enough to allow study through transmission of an illumination beam, e.g., an infrared illumination beam, through the sample 1481 (i.e. in transmission mode), or the sample 1481 can be an optically opaque sample that is analyzed through reflection of an illumination beam, e.g., an infrared illumination beam, by the sample (i.e. in reflection mode). For example, in the embodiment illustrated in FIG. 14, the imaging microscope 1483 can alternatively be utilized in both transmission mode and reflection mode.

The design of the imaging microscope 1483 can be varied. In the embodiment illustrated in FIG. 14, the imaging microscope 1483 includes (i) two of the laser sources 1410 that are similar to the laser sources described above; (ii) a stage assembly 1485 that retains and positions the sample 1410, (iii) an imaging lens assembly 1487 (e.g., one or more lenses 1487A, 1487B), and (iv) an image sensor 1489 that converts an optical image into an array of electronic signals. The design of each of these components can be varied pursuant to the teachings provided herein.

In one embodiment, the laser sources 1410 each emits a temporally coherent, illumination beam that is usable for illuminating and analyzing the sample 1481 in transmission mode; and/or (ii) emits a temporally coherent, illumination beam that is usable for illuminating and analyzing the sample 1481 in reflection mode.

A suitable imaging microscope 1483 is described in more detail in PCT Application No. PCT/US2012/061987, having an international filing date of Oct. 25, 2012, entitled "Infrared Imaging Microscope Using Tunable Laser Radiation". As far as permitted, the contents of PCT/US2012/061987, are incorporated herein by reference.

While the particular systems as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A laser source for emitting an output beam directed along an output axis, the laser source comprising:
    a first laser module that generates a first beam when power is directed to the first laser module;
    a second laser module that generates a second beam when power is directed to the second laser module;
    a beam selector assembly that includes a beam selector, and a selector mover that selectively moves the beam selector between a first position in which the first beam is directed along the output axis, and a second position in which the second beam is directed along the output axis;
    a first director assembly that directs the first beam at the beam selector when the beam selector is in the first position, the first director assembly including a pair of spaced apart, first redirectors that are independently adjustable to reflect and redirect the first beam at the beam selector when the beam selector is in the first position;
    a second director assembly that directs the second beam at the beam selector when the beam selector is in the second position, the second director assembly including a pair of spaced apart, second redirectors that are independently adjustable to reflect and redirect the second beam at the beam selector when the beam selector is in the second position, wherein each second redirector is independently adjustable relative to each first redirector; and
    a control system that selectively directs power to the first laser module and the second laser module.

2. The laser source of claim 1 wherein each redirector is independently adjustable about two axes.

3. The laser source of claim 1 wherein the beam selector includes a mirror having a mirror center; wherein the first director assembly directs the first beam approximately at the mirror center when the beam selector is in the first position; and wherein the second director assembly directs the second beam approximately at the mirror center when the beam selector is in the second position; and wherein the selector mover moves the beam selector about a selector pivot axis.

4. The laser source of claim 1 further comprising (i) a third laser module that generates a third beam; (ii) a fourth laser module that generates a fourth beam; (iii) a third director assembly that directs the third beam at the beam selector when the beam selector is in a third position; and (iv) a fourth director assembly that directs the fourth beam at the beam selector when the beam selector is in a fourth position; wherein the selector mover selectively moves the beam selector to the third position in which the third beam is directed along the output axis with the beam selector, and the fourth position in which the fourth beam is directed along the output axis with the beam selector.

5. The laser source of claim 1 wherein (i) the first beam has a center wavelength in the MIR range; and (ii) the second beam has a center wavelength in the MIR range.

6. The laser source of claim 1 wherein the beam selector assembly includes a galvo.

7. The laser source of claim 1 (i) wherein the first laser module includes a first gain medium that generates the first beam, a first grating, a first grating mover that selectively moves the first grating to select the desired wavelength of the first beam, and a first feedback detector that provides a first feedback signal that relates to an angle of incidence of the first beam on the first grating; (ii) wherein the second laser module includes a second gain medium that generates the second beam, a second grating, a second grating mover that selectively moves the second grating to select the desired wavelength of the second beam, and a second feedback detector that provides a second feedback signal that relates to an angle of incidence of the second beam on the second grating; and (iii) wherein the control system selectively directs pulses of power to the first gain medium based on the first feedback signal, and selectively directs pulses of power to the second gain medium based on the second feedback signal.

8. The laser source of claim 7 wherein the first feedback detector includes a plurality of encoder marks and an optical reader that monitors the encoder marks; and wherein the control system selectively directs a pulse of power to the first gain medium whenever the optical reader reads a predetermined number of encoder marks.

9. The laser source of claim 7 wherein the control system determines a center wavelength of the output beam based on the feedback signal.

10. An assembly including the laser source of claim 1 that directs the output beam at a sample, and a spectrometer.

11. The laser source of claim 1 further comprising a frame base that retains the first laser module and the second laser module; wherein the first laser module includes a first module frame and a first temperature controller that is positioned between the first module frame and the frame base, the first temperature controller controlling the temperature of the first laser module; and wherein the second laser module includes a second module frame and a second temperature controller that is positioned between the second module frame and the frame base, the second temperature controller controlling the temperature of the second laser module.

12. The laser source of claim 11 (i) wherein the first laser module includes a first gain medium that generates the first beam, a first grating, and a first grating mover that selectively moves the first grating to select the desired wavelength of the first beam; (ii) wherein the first gain medium, the first grating, and the first grating mover are secured to the first module frame; and (iii) wherein the first module frame cantilevers away from the first temperature controller.

13. The laser source of claim 1 further comprising a source frame that defines a first chamber and a spaced apart second chamber, the source frame including a floor aperture, and a pass through electrical connector that is positioned in the floor aperture and that is sealed to the source frame, wherein the laser modules are positioned in the first chamber, and at least portion of the control system is positioned in the second chamber; and wherein the control system is electrically connected to the laser modules via the pass through electrical connector.

14. The laser source of claim 1 (i) wherein the first laser module includes a first gain medium that generates the first beam, a first wavelength dependent feedback device, and a first feedback detector that provides a first feedback signal that relates to the first wavelength dependent feedback device; (ii) wherein the second laser module includes a second gain medium that generates the second beam, a second wavelength dependent feedback device, and a second feedback detector that provides a second feedback signal that relates to the second wavelength dependent feedback device; and (iii) wherein the control system selectively directs pulses of power to the first gain medium based on the first feedback signal, and selectively directs pulses of power to the second gain medium based on the second feedback signal.

15. A microscope that is used to analyze a sample, the microscope comprising: a stage that retains the sample, and the laser source of claim 1 that directs the output beam at the sample.

16. A method for generating an output beam directed along an output axis, the method comprising the steps of:
generating a first beam with a first laser module;
generating a second beam with a second laser module;
selectively moving a beam selector between a first position in which the first beam is directed along the output axis, and a second position in which the second beam is directed along the output axis;
directing the first beam at the beam selector when the beam selector is in the first position with a first director assembly, the first director assembly including a pair of spaced apart, first redirectors that are independently adjustable to reflect and redirect the first beam at the beam selector when the beam selector is in the first position; and
directing the second beam at the beam selector when the beam selector is in the second position with a second director assembly, the second director assembly including a pair of spaced apart, second redirectors that are independently adjustable to reflect and redirect the second beam at the beam selector when the beam selector is in the second position, wherein each second redirector is independently adjustable relative to each first redirector.

17. The method of claim 16 wherein each redirector is independently adjustable about two axes.

18. A laser source for emitting an output beam directed along an output axis, the laser source comprising:
a first laser module that generates a first beam when power is directed to the first laser module;
a second laser module that generates a second beam when power is directed to the second laser module;
a beam selector assembly that includes a beam selector, and a selector mover that selectively moves the beam selector between a first position in which the first beam is directed along the output axis, and a second position in which the second beam is directed along the output axis, the beam selector including a mirror that is moved by the selector mover between a first position and a second position, the mirror having a mirror center;
a first director assembly that includes a pair of spaced apart, first redirectors that are independently adjustable about two axes to reflect and redirect the first beam approximately at the mirror center of the mirror when the mirror is in the first position;
a second director assembly that includes a pair of spaced apart, second redirectors that are independently adjustable about two axes to reflect and redirect the second beam approximately at the mirror center of the mirror when the mirror is in the second position; and
a control system that selectively directs power to the first laser module and the second laser module.

19. The laser source of claim 18 (i) wherein the first laser module includes a first gain medium that generates the first beam, a first grating, a first grating mover that selectively moves the first grating to select the desired wavelength of the first beam, and a first feedback detector that provides a first feedback signal that relates to an angle of incidence of the first beam on the first grating; (ii) wherein the second laser module includes a second gain medium that generates the second beam, a second grating, a second grating mover that selectively moves the second grating to select the desired wavelength of the second beam, and a second feedback detector that provides a second feedback signal that relates to an angle of incidence of the second beam on the second grating; and (iii) wherein the control system selectively directs pulses of power to the first gain medium based on the first feedback signal, and selectively directs pulses of power to the second gain medium based on the second feedback signal.

20. A microscope that is used to analyze a sample, the microscope comprising: a stage that retains the sample, and the laser source of claim 18 that directs the output beam at the sample.

* * * * *